(12) United States Patent
Delmonte et al.

(10) Patent No.: US 11,919,863 B2
(45) Date of Patent: Mar. 5, 2024

(54) SUBSTITUTED QUINOLINYLCYCLOHEXYLPROPANAMIDE COMPOUNDS AND IMPROVED METHODS FOR THEIR PREPARATION

(71) Applicant: BRISTOL-MYERS SQUIBB COMPANY, Princeton, NJ (US)

(72) Inventors: Albert J. Delmonte, Princeton, NJ (US); Benjamin M. Cohen, Princeton, NJ (US); Kenneth Joseph Fraunhoffer, Princeton, NJ (US); Sergei Kolotuchin, Princeton, NJ (US); Francisco Gonzalez-Bobes, Princeton, NJ (US); Gregory Louis Beutner, Princeton, NJ (US); Adam Joseph Freitag, Princeton, NJ (US); Michael Scott Bultman, Portage, MI (US); Yu Fan, Highland Park, NJ (US); Prantik Maity, Bangalore (IN); Ian Scott Young, Redwood City, CA (US); Hilary Plake Beck, Emerald Hills, CA (US); Maksim Osipov, Redwood City, CA (US); Jay Patrick Powers, Pacifica, CA (US); Maureen Kay Reilly, Burlingame, CA (US); Hunter Paul Shunatona, Oakland, CA (US); James Ross Walker, Verona, WI (US); Mikhail Zibinsky, Redwood City, CA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 17/552,929

(22) Filed: Dec. 16, 2021

(65) Prior Publication Data
US 2022/0267273 A1 Aug. 25, 2022

Related U.S. Application Data

(62) Division of application No. 16/624,448, filed as application No. PCT/US2018/040276 on Jun. 29, 2018, now Pat. No. 11,236,048.

(60) Provisional application No. 62/649,155, filed on Mar. 28, 2018, provisional application No. 62/527,821, filed on Jun. 30, 2017, provisional application No. 62/527,835, filed on Jun. 30, 2017.

(51) Int. Cl.
| C07D 215/18 | (2006.01) |
| C07C 51/09 | (2006.01) |
| C07C 67/333 | (2006.01) |
| C07C 67/343 | (2006.01) |

(52) U.S. Cl.
CPC ............ *C07D 215/18* (2013.01); *C07C 51/09* (2013.01); *C07C 67/333* (2013.01); *C07C 67/343* (2013.01)

(58) Field of Classification Search
None
See application file for complete search history.

(56) References Cited

U.S. PATENT DOCUMENTS

| 9,598,422 | B2 | 3/2017 | Beck et al. |
| 9,643,972 | B2 | 5/2017 | Beck et al. |
| 2001/0041700 | A1 | 11/2001 | Bekkali et al. |
| 2004/0171614 | A1 | 9/2004 | Pissarnitski et al. |
| 2010/0056576 | A1 | 3/2010 | Burger et al. |
| 2015/0126490 | A1 | 5/2015 | Bagdanoff et al. |
| 2016/0137652 | A1* | 5/2016 | Beck ............... C07D 401/14 546/139 |
| 2019/0282714 | A1 | 9/2019 | Donnelly et al. |

FOREIGN PATENT DOCUMENTS

| JP | S53149910 A | 12/1978 |
| JP | S57085338 A | 5/1982 |
| JP | 2002509126 A | 3/2002 |
| JP | 2007-519607 A | 7/2007 |
| JP | 2008019177 A | 1/2008 |
| JP | 2008019178 A | 1/2008 |
| JP | 2012-501314 A | 1/2012 |
| JP | 2016-540728 A | 12/2016 |
| JP | 2020-526520 A | 8/2020 |
| JP | 6987840 B2 | 1/2022 |
| WO | 1999036381 A1 | 7/1999 |
| WO | 2008007582 A1 | 1/2008 |
| WO | 2008007589 A1 | 1/2008 |
| WO | 2012/050159 A1 | 4/2012 |
| WO | 2015/184099 A1 | 12/2015 |
| WO | 2016/073770 A1 | 5/2016 |
| WO | 2016/073774 A2 | 5/2016 |
| WO | 2018/017529 A1 | 1/2018 |
| WO | 2018/039512 A1 | 3/2018 |

OTHER PUBLICATIONS

Brandacher et al., "Prognostic Value of Indoleamine 2,3-Dioxygenase Expression in Colorectal Cancer: Effect on Tumor-Infiltrating T Cells", Clin. Cancer Res., Feb. 2006, 12(4), 1144-1151.
Gartner, P. et al. "Lithium tri-sec-butylborodeuteride: a new reagent for the stereoselective deuterium addition to cyclohexanones with single chair conformations" ARKIVOC 2001 (ii) 9-20 (Year: 2001).
ISA/US, PCT International Search Report and Written Opinion for PCT/US18/40276, dated Nov. 29, 2018.
PubChem, "2-[4-(6-Fluoroquinolin-4-yl)cyclohexyl]acetic acid", PubChem CID: 121318150, Aug. 6, 2016, p. 4, Fig., 14 pages.
4th Series of Experimental Chemistry, 1992.

(Continued)

*Primary Examiner* — Medhanit W Bahta
(74) *Attorney, Agent, or Firm* — BakerHostetler

(57) ABSTRACT

The disclosure is directed to improved methods for preparing substituted quinolinylcyclohexylpropanamide compounds.

17 Claims, No Drawings

(56) References Cited

OTHER PUBLICATIONS

U.S. Appl. No. 16/624,448, filed Dec. 19, 2019.
Japanese Office Action (with English Translation) for Application No. JP 2019-572564 dated Jan. 17, 2023.
Carruthers, W. et al., Modern Methods of Organic Synthesis, 4th edition, East China University of Science and Technology Press, Mar. 2006, pp. 438-439.

* cited by examiner

SUBSTITUTED QUINOLINYLCYCLOHEXYLPROPANAMIDE COMPOUNDS AND IMPROVED METHODS FOR THEIR PREPARATION

CROSS-REFERENCE TO RELATED APPLICATIONS

This application is a divisional of U.S. application Ser. No. 16/624,448, filed Dec. 19, 2019, now U.S. Pat. No. 11,236,048, which is the National Stage Application of International Patent Application No. PCT/US2018/040276, filed Jun. 29, 2018, which claims the benefit of U.S. Provisional Application No. 62/527,821, filed Jun. 30, 2017, U.S. Provisional Application No. 62/527,835, filed Jun. 30, 2017, and U.S. Provisional Application No. 62/649,155, filed Mar. 28, 2018, the entireties of which are incorporated by reference herein.

TECHNICAL FIELD

The disclosure is directed to improved methods for preparing substituted quinolinylcyclohexylpropanamide compounds.

BACKGROUND

Indoleamine 2,3-dioxygenase (IDO; also known as IDO1) is an IFN-γ target gene that plays a role in immunomodulation. IDO plays a major role in immune regulation, and its immunosuppressive function manifests in several manners. A pathophysiological link exists between IDO and cancer. Disruption of immune homeostasis is intimately involved with tumor growth and progression, and the production of IDO in the tumor microenvironment appears to aid in tumor growth and metastasis. Moreover, increased levels of IDO activity are associated with a variety of different tumors (Brandacher, G. et al., *Clin. Cancer Res.*, 12(4):1144-1151 (Feb. 15, 2006)). In addition to cancer, IDO has been implicated in, among other conditions, immunosuppression, chronic infections, and autoimmune diseases or disorders (e.g., rheumatoid arthritis).

Substituted quinolinylcyclohexylpropanamide pharmaceutical compounds that inhibit IDO and are useful for the treatment of cancer have been previously described. See, e.g., WO2016/073770. Improved methods of making such compounds, which reduce production costs and improve production safety, are, therefore, needed.

SUMMARY

The disclosure is directed to methods of making compounds of formula I, or stereoisomers thereof:

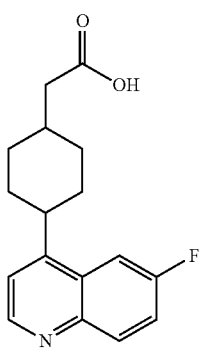

I comprising
contacting a compound of formula II, or a stereoisomer thereof:

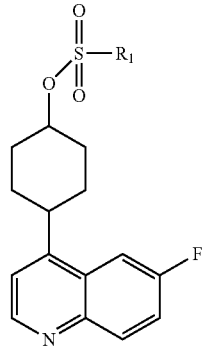

II wherein $R_1$ is $C_{1-6}$alkyl, aryl, or $C_{1-6}$haloalkyl;
with a mixture of a $C_{1-6}$alkoxide salt and a di-$C_{1-6}$alkyl-malonate, in a suitable organic solvent;
for a time and at a temperature sufficient to displace the sulfonate moiety and to produce a compound of formula III, or a stereoisomer thereof:

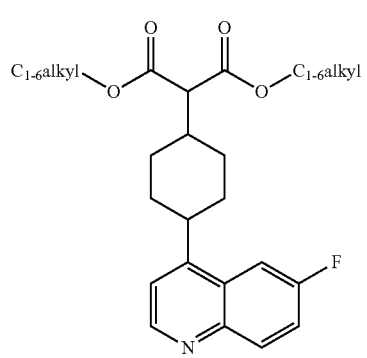

III and
contacting the compound of formula III, or a stereoisomer thereof, with a suitable organic acid, in a suitable aqueous solvent, for a time and at a temperature sufficient for hydrolysis and decarboxylation and to produce the compound of formula I, or a stereoisomer thereof.

Methods of making intermediate compounds, such as compounds of formula II, and stereoisomers thereof, are also described.

Substituted quinolinylcyclohexylpropanamide compounds, as well as substituted quinolinylcyclohexylpropanamide compounds prepared according to the described methods are also described.

DETAILED DESCRIPTION OF ILLUSTRATIVE EMBODIMENTS

The disclosure may be more fully appreciated by reference to the following description, including the following glossary of terms and the concluding examples. It is to be appreciated that certain features of the disclosed compositions and methods which are, for clarity, described herein in the context of separate aspects, may also be provided in combination in a single aspect. Conversely, various features of the disclosed compositions and methods that are, for brevity, described in the context of a single aspect, may also be provided separately or in any subcombination.

As used herein, "alkyl" includes both branched and straight-chain saturated aliphatic hydrocarbon groups having the specified number of carbon atoms. For example, "$C_1$-$C_6$ alkyl" or "$C_{1-6}$ alkyl" denotes alkyl having 1 to 6 carbon atoms. Example alkyl groups include, but are not limited to, methyl (Me), ethyl (Et), propyl (e.g., n-propyl and isopropyl), butyl (e.g., n-butyl, isobutyl, r-butyl), and pentyl (e.g., n-pentyl, isopentyl, neopentyl).

When a range of carbon atoms is used herein, for example, $C_{1-6}$, all ranges, as well as individual numbers of carbon atoms are encompassed. For example, "$C_{1-3}$" includes $C_{1-3}$, $C_{1-2}$, $C_{2-3}$, $C_1$, $C_2$, and $C_3$.

As used herein, "haloalkyl" includes both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

The term "cycloalkyl" refers to cyclized alkyl groups. $C_{3-6}$ cycloalkyl is intended to include $C_3$, $C_4$, $C_5$, and $C_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalkenyl groups. Example cycloalkenyl groups include, but are not limited to, cyclobutenyl, cyclopentenyl, and cyclohexenyl.

The term "heterocycloalkyl" refers to any five to ten membered monocyclic or bicyclic, saturated ring structure containing at least one heteroatom selected from the group consisting of O, N and S. The heterocycloalkyl group may be attached at any heteroatom or carbon atom of the ring such that the result is a stable structure. Examples of suitable heterocycloalkyl groups include, but are not limited to, azepanyl, aziridinyl, azetidinyl, pyrrolidinyl, dioxolanyl, imidazolidinyl, pyrazolidinyl, piperazinyl, piperidinyl, dioxanyl, morpholinyl, dithianyl, thiomorpholinyl, oxazepanyl, oxiranyl, oxetanyl, quinuclidinyl, tetrahydrofuranyl, tetrahydropyranyl, piperazinyl, and the like.

As used herein, "alkoxy" refers to an —O-alkyl group.

As used herein, "aryl" refers to an aromatic ring system which includes, but not limited to phenyl, biphenyl, indanyl, 1-naphthyl, 2-naphthyl and tetrahydronaphthyl.

As used herein, "heteroaryl" refers to refers to aryl mono- or bicyclic rings that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom or through a carbon atom. Non-limiting examples of heteroaryl groups include pyridyl, pyridazinyl, pyrazinyl, pyrimidinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, fury, thienyl and the like.

As used herein, "halo" or "halogen" includes fluoro, chloro, bromo, and iodo.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, aspartic, propionic, succinic, glycolic, stearic, lactic, malic (e.g., L-malic), tartaric, citric, ascorbic, pamoic, maleic, hydroxymaleic, phenylacetic, glutamic, benzoic, salicylic, sulfanilic, 2-acetoxybenzoic, fumaric, p-toluenesulfonic, methanesulfonic, ethane disulfonic (e.g., ethane-1, 2-disulfonic), oxalic, isethionic, naphthalene-1,5-disulfonic, naphthalene-2-disulfonic, benzenesulfonic, gluconic, hippuric, glutaric, carbonic, isobutyric, malonic, suberic, mandelic, phthalic, camphorsulfonic, and the like.

The compounds of the present invention may also contain unnatural proportions of one, two, three, or more atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as, for example, tritium ($^3$H), iodine-125 ($^{125}$I), fluorine-18 ($^{18}$F), and/or carbon-14 ($^{14}$C), or non-radioactive isotopes, such as deuterium ($^2$H), carbon-13 ($^{13}$C), and/or nitrogen-15 ($^{15}$N). Such isotopic variations can provide additional utilities to those described elsewhere within this application. For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics which can contribute to enhanced safety, tolerability or efficacy during treatment. All isotopic variations of the compounds of the present invention, whether radioactive or not, are intended to be encompassed within the scope of the present invention.

Also included within the scope of the disclosure are co-crystals of the compounds of the disclosure, for example, co-crystals including Compound 1. Exemplary co-crystal formers include amino acids, for example, co-crystals prepared with proline, glycine, alanine, histidine, arginine, lysine, and the like. Other exemplary co-crystal formers include sugars, for example, monosaccharides such as glucose and fructose. Other co-crystal formers include sugar alcohols such as, for example, mannitol and sorbitol. Amides are other suitable co-crystal formers and include, for example, urea, nicotinamide, and isonicotinamide. Amines are also suitable co-crystal formers and include, for example, imidazole and N-meglumine.

The pharmaceutically acceptable salts and co-crystals of the present invention can be synthesized from the parent compound that contains a basic or acidic moiety by conventional chemical methods. Generally, such salts and co-crystals can be prepared by reacting the free acid or base forms of these compounds with a stoichiometric amount of the appropriate base or acid or co-crystal former in water or in an organic solvent, or in a mixture of the two; generally, nonaqueous media like ether, ethyl acetate, ethanol, isopropanol, or acetonitrile are preferred. See, e.g., Allen, Jr., L. V., ed., *Remington: The Science and Practice of Pharmacy*, 22nd Edition, Pharmaceutical Press, London, UK (2012). The disclosure of which is hereby incorporated by reference.

The following acronyms and abbreviations are used in the disclosure:

HPLC=high performance liquid chromatography
PEPPSI™-IPr=[1,3-Bis(2,6-Diisopropylphenyl)imidazol-2-ylidene](3-chloropyridyl)palladium(II) dichloride
Ms=mesyl (—S(O)$_2$—O—CH$_3$)
MsCl=mesyl chloride (Cl—S(O)$_2$—O—CH$_3$)
DME=dimethoxyethane
dr=diastereomeric ratio
PivCl=pivaloyl chloride (trimethylacetyl chloride)
AcOH=acetic acid
NaHMDS=hexamethyldisilazane sodium salt (sodium bis(trimethylsilyl)amide)
T3P™=propylphosphonic anhydride (2,4,6-Tripropyl-1,3,5,2,4,6-trioxatriphosphorinane-2,4,6-trioxide solution)
DMAC=dimethylacetamide
MeCN=acetonitrile (ACN)
NMP=N-methyl-2-pyrrolidone
Pyr=pyridine
TCFH=N,N,N',N'-tetramethylchloroformamidinium hexafluorophosphate
N-Me-IMid=N-methylimidazole
KF=Karl Fischer titration analysis, a titration method to determine the amount of water in a sample.

The disclosure is directed to improved methods for the preparation of compounds of formula I, as well as stereoisomers thereof, as well as salts thereof:

I

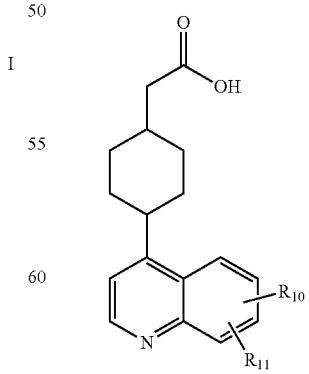

Preferred stereoisomers of formula I include

I-A

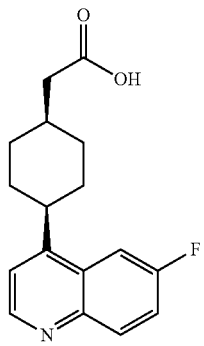

and

I-B

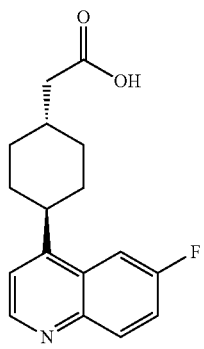

The compounds of formula I can be produced as a single stereoisomer, for example, I-A or I-B. Alternatively, the compounds of formula I can be produced as a mixture of I-A and I-B. In those embodiments employing a mixture of stereoisomers, that is, a mixture of I-A and I-B, the mixture can comprise 99 wt. % of I-A. Alternatively, the mixture can comprise about 95 wt. %, 90 wt. %, 85 wt. %, 80 wt. %, 75 wt. %, 70 wt. %, 65 wt. %, 60 wt. %, 55 wt. %, 50 wt. %, 45 wt. %, 40 wt. %, 35 wt. %, 30 wt. %, 25 wt. %, 20 wt. %, 15 wt. %, 10 wt. %, or about 5 wt. % of I-A.

Those of ordinary skill in the art will readily appreciate that the methods described herein can also be used to prepare compounds of formula I-A, as well as stereoisomers thereof, as well as salts thereof

I-C wherein $R_{10}$ and $R_{11}$ are independently hydrogen, halogen, $C_{1-4}$haloalkyl, $C_{3-6}$cycloalkyl, $C_{3-6}$heterocycloalkyl, phenyl, heteroaryl, $C_{1-4}$alkyl, $C_{1-4}$alkoxy, CN, —$SO_2NH_2$, $NHSO_2CH_3$, $NHSO_2CF_3$, $OCF_3$, $SO_2CH_3$, $SO_2CF_3$, or $CONH_2$.

The compounds of formula I (or the stereoisomers or salts thereof) can be prepared according to Scheme 1:

Scheme 1

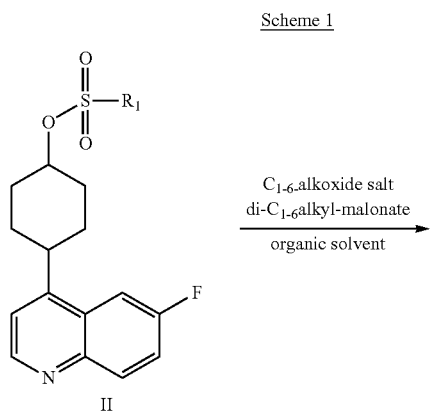

II

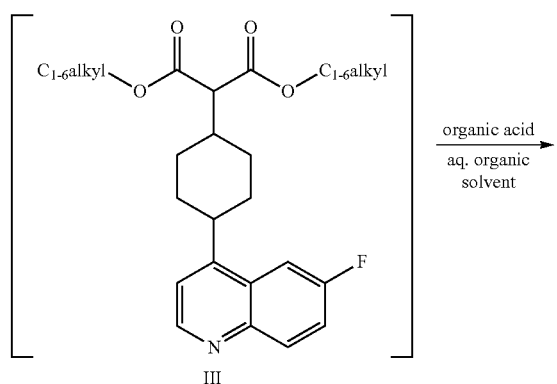

III

According to the disclosure, compounds of formula I, or a stereoisomer thereof, or a salt thereof, are prepared by contacting a compound of formula II, or a stereoisomer thereof

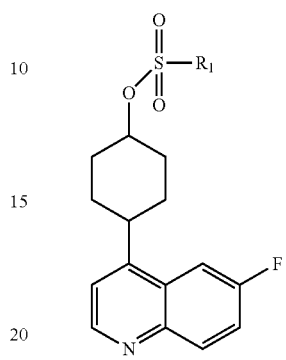

II wherein $R_1$ is $C_{1-6}$alkyl, aryl, or $C_{1-6}$haloalkyl; with a mixture of a $C_{1-6}$alkoxide salt and a di-$C_{1-6}$alkyl-malonate, in a suitable organic solvent, for a time and at a temperature sufficient to displace the sulfonate moiety and to produce a compound of formula III, or a stereoisomer thereof:

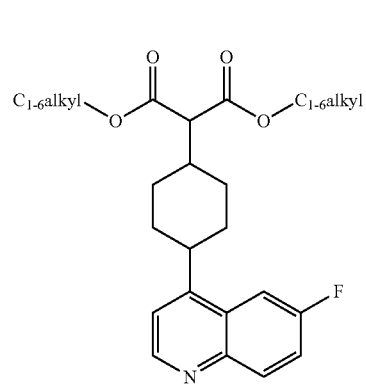

III

The compound of formula II can be a single stereoisomer or a mixture of stereoisomers. For example, the compound of formula II can be provided as a single isomer that is

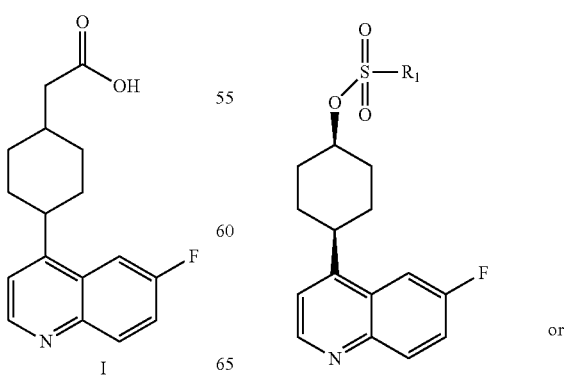

II-A or

-continued

II-B

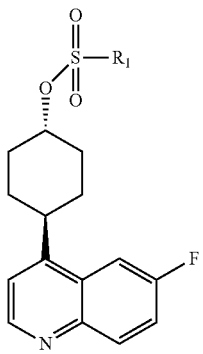

Alternatively, the compound of formula II can be provided as a mixture of II-A and II-B. In those embodiments employing a mixture of stereoisomers, that is, a mixture of II-A and II-B, the mixture can comprise 99 wt. % of II-B. Alternatively, the mixture can comprise about 95 wt. %, 90 wt. %, 85 wt. %, 80 wt. %, 75 wt. %, 70 wt. % 65 wt. %, 60 wt. %, 55 wt. %, 50 wt. %, 45 wt. %, 40 wt. %, 35 wt. %, 30 wt. %, 25 wt. %, 20 wt. %, 15 wt. %, 10 wt. %, or about 5 wt. % of II-B.

The compound of formula III can be produced as a single isomer or as a mixture of stereoisomers. For example, the compound of formula III can be produced as a single isomer that is

III-A or

III-B

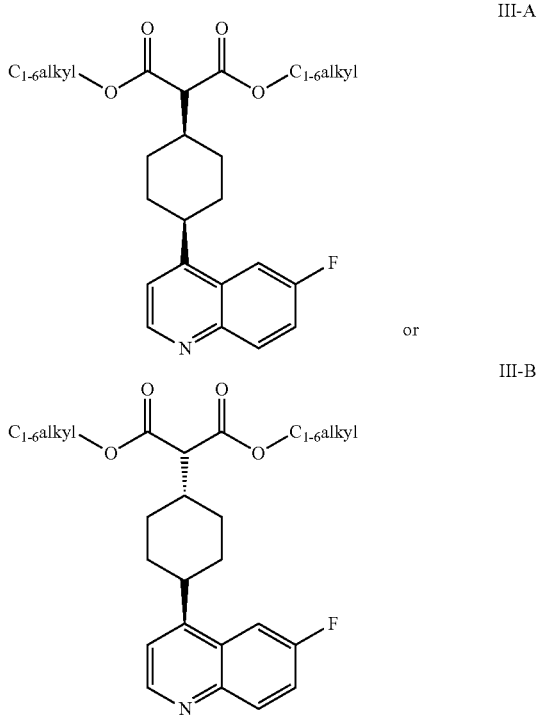

Alternatively, the compound of formula III can be provided as a mixture of III-A and III-B. In those embodiments employing a mixture of stereoisomers, that is, a mixture of III-A and III-B, the mixture can comprise 99 wt. % of III-A. Alternatively, the mixture can comprise about 95 wt. %, 90 wt. %, 85 wt. %, 80 wt. %, 75 wt. %, 70 wt. %, 65 wt. %, 60 wt. %, 55 wt. %, 50 wt. %, 45 wt. %, 40 wt. %, 35 wt. %, 30 wt. %, 25 wt. %, 20 wt. %, 15 wt. % 10 wt. %, or about 5 wt. % of III-A.

According to the disclosure, $R_1$ can be $C_{1-6}$alkyl, for example, methyl, ethyl, propyl, isopropyl, butyl, s-butyl, t-butyl, pentyl, or hexyl. In preferred aspects, $R_1$ is methyl.

In other aspects, $R_1$ is aryl. In some embodiments, $R_1$ is phenyl. In other embodiments, $R_1$ is substituted phenyl, for example, phenyl substituted with halo (e.g., F or Cl), $C_{1-6}$alkyl (e.g., methyl, ethyl, propyl, isopropyl, butyl, s-butyl, t-butyl), or $C_{1-6}$haloalkyl (e.g., —$CF_3$, —$CHF_2$, —$CH_2F$, or —$CH_2CF_3$).

In other aspects, $R_1$ is $C_{1-6}$haloalkyl for example, —$CF_3$, —$CHF_2$, —$CH_2F$, or —$CH_2CF_3$.

The conversion of compounds of formula II to compounds of formula III employs a $C_{1-6}$alkoxide salt. A preferred $C_{1-6}$alkoxide salt is sodium amylate (NaOC(CH$_3$)$_2$CH$_2$CH$_3$). Other suitable $C_{1-6}$alkoxide salts include potassium amylase, NaOBu$^t$, and KOBu$^t$. Other $C_{1-6}$alkoxide salts include lithium amylate and LiOBu$^t$.

The conversion of compounds of formula II to compounds of formula III employs a mixture of the $C_{1-6}$alkoxide salt with a di-$C_{1-6}$alkyl-malonate. According to the disclosure, the $C_{1-6}$alkyl moieties on the malonate are independently selected. For example, in some aspects, the $C_{1-6}$alkyl moieties in the di-$C_{1-6}$alkyl-malonate are the same, e.g., di-tert-butyl-malonate, di-methyl-malonate, di-ethyl-malonate, di-isopropyl-malonate. In other aspects, the $C_{1-6}$alkyl moieties in the di-$C_{1-6}$alkyl-malonate are different, e.g. CH$_3$OC(O)CH$_2$C(O)OBu$^t$.

In preferred embodiments, the molar ratio of the $C_{1-6}$alkoxide salt to the di-$C_{1-6}$alkyl-malonate is about 1:1. In other embodiments, the molar ratio of the $C_{1-6}$alkoxide salt to the di-$C_{1-6}$alkyl-malonate is about 0.5:1 to about 1.5:1, for example, about 0.5:1, 0.6:1, 0.7:1, 0.8:1, 0.9:1, 1:1, 1.1:1, 1.2:1, 1.3:1, 1.4:1, or about 1.5:1. Exemplary molar ratios of the $C_{1-6}$alkoxide salt to the di-$C_{1-6}$alkyl-malonate are about 0.8:1 to 1.2:1 or about 0.8:1 to 1.1:1.

In preferred embodiments an equivalent amount or an excess of the $C_{1-6}$alkoxide salt and the di-$C_{1-6}$alkyl-malonate relative to the compound of formula II is employed. For example, in exemplary embodiments, the molar ratio of the $C_{1-6}$alkoxide salt and the di-$C_{1-6}$ alkyl-malonate relative to the compound of formula II about 1.5:1. In other embodiments, the molar ratio of the $C_{1-6}$alkoxide salt and the di-$C_{1-6}$alkyl-malonate relative to the compound of formula II about 1:1 to about 3:1, for example, about 1:1, 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5:1, 2.6:1, 2.7:1, 2.8:1, 2.9:1, or about 3:1.

The conversion of compounds of formula II to compounds of formula III is conducted in a suitable organic solvent. Mixtures of organic solvents can also be employed. Suitable organic solvents for the conversion include, for example, aromatic hydrocarbons such as toluene and anisole, with toluene being particularly preferred. Other suitable solvents include ethereal solvents, such as, for example, tetrahydrofuran, dimethoxyethane, and dioxane. The conversion can also be conducted in a polar solvent, for example, t-amyl alcohol, or N-methyl-2-pyrrolidone.

The conversion of compounds of formula II to compounds of formula III is conducted at a temperature sufficient to displace the sulfonate moiety of a compound of formula II to produce a compound of formula III. Those of skill in the art will readily be able to ascertain an appropriate temperature, using the methods described herein in combination with the knowledge in the art. Preferably, the reaction temperatures are above ambient temperature, that is, above 25° C., preferably about 35° C., or above. For example, suitable temperatures for conversion to a compound of formula III are temperatures that are at or below the reflux temperature of the reaction solvent. In other aspects, a suitable temperature for conversion to a compound of formula III is a temperature below the reflux temperature of the reaction solvent. In other aspects, temperatures of about 80° C., or higher are preferred. As used herein, the temperature refers to the internal temperature of the reaction mixture.

Those of ordinary skill in the art, using the methods described herein in combination with the knowledge in the art, will be readily able to ascertain an appropriate amount of time for the conversion of compounds of formula II to compounds of formula III. For example, the conversion can be conducted until the conversion is substantially complete, as determined by HPLC. In some aspects, the amount of time for substantial conversion to compounds of formula III is about 24 hours. In other aspects, the amount of time for substantial conversion is less than 24 hours, for example, about 20, 18, 16, 14, 12, 10, or about 8 hours. In still other aspects, the amount of time for substantial conversion is less than 8 hours. In preferred embodiments, the amount of time for substantial conversion is about 12 hours.

The methods described herein produce a compound of formula III, or a stereoisomer thereof. The $C_{1-6}$alkyl groups of the compound of formula III can be the same or different. Preferred compounds of formula III are those wherein each $C_{1-6}$alkyl is t-butyl. In other aspects, one $C_{1-6}$alkyl is t-butyl and the other is —$C(CH_3)_2CH_2CH_3$.

In preferred embodiments of the disclosure, the compound of formula III is not isolated and is used without isolation or purification for further conversion reactions. Alternatively, the compound of formula III can be isolated, and optionally purified, using methods known in the art.

According to the disclosure, a compound of formula III, or a stereoisomer thereof, can be convened to a compound of formula I, or a stereoisomer thereof, by contacting the compound of formula III with a suitable organic acid, in a suitable aqueous organic solvent, for a time and at a temperature sufficient for hydrolysis and decarboxylation, to produce the compound of formula I, or a stereoisomer thereof.

Suitable organic acids for the conversion of the compound of formula III to a compound of formula I include, for example, sulfonic acids such as methanesulfonic acid, which is particularly preferred. Trifluoroacetic acid is also a suitable acid. Preferably, the acid will have a pKa that is less than or equal to 0. In other embodiments, the compound of formula III is convened to the compound of formula I by contacting the compound of formula III with a mineral acid such as $H_2SO_4$.

In preferred embodiments, a molar excess of the organic acid, relative to the compound of formula III is used. For example, the molar ratio of the organic acid to the compound of formula III is about 2:1 to about 20:1 or about 8:1 to about 10:1, e.g., about 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, or about 20:1.

The solvent for the conversion of the compound of formula III to the compound of formula I is an aqueous organic solvent, that is, the solvent contains at least 0.05 wt. %, by weight of the solvent, of water. Preferably, the aqueous solvent contains about 1 wt. % of water. In addition to water, the aqueous solvent includes a single organic solvent or a mixture of organic solvents, preferably a mixture of organic solvents. In some aspects, the solvent is an aromatic hydrocarbon (e.g., toluene, anisole), an ethereal solvent (e.g., tetrahydrofuran, dimethoxyethane, dioxane), or a polar solvent (e.g., t-amyl alcohol, N-methyl-2-pyrrolidone, sulfolane), or a mixture thereof. In some aspects, the aqueous solvent is a mixture of water, sulfolane, and another organic solvent, preferably toluene.

The conversion of compounds of formula III to compounds of formula I is conducted at a temperature sufficient for hydrolysis and decarboxylation of the compound of formula III to produce a compound of formula I. Those of skill in the art will readily be able to ascertain an appropriate temperature, using the methods described herein in combination with the knowledge in the art. Preferred temperatures are those that are above 25° C. In some aspects, a single temperature can effect both hydrolysis, as well as decarboxylation. In other aspects, hydrolysis is conducted at one temperature and decarboxylation is conducted at another temperature. In those embodiments employing different temperatures for hydrolysis and decarboxylation, the hydrolysis can be conducted at a lower temperature (e.g., between about 30° C. and about 80° C., preferably between about 40° C. and about 60° C.) and the decarboxylation can be conducted at a higher temperature (e.g. between about 90° C. and about 115° C. preferably between about 100° C. and about 110° C. with about 105° C. being particularly preferred). As used herein, the temperature refers to the internal temperature of the reaction mixture.

Those of ordinary skill in the art, using the methods described herein in combination with the knowledge in the art, will be readily able to ascertain an appropriate amount of time for the conversion of compounds of formula III to compounds of formula I. For example, the conversion can be conducted until the conversion is substantially complete, as determined by HPLC. In some aspects, the amount of time for substantial conversion to formula I is about 30 hours. In other aspects, the amount of time for substantial conversion is about 24 hours or less, for example, about 24, 22, 20, 18, 16, 14, 12, 10, or about 8 hours. In still other aspects, the amount of time for substantial conversion is less than 8 hours. In preferred embodiments, the amount of time for substantial conversion is about 15 hours. In those aspects wherein the hydrolysis is conducted at one temperature and the decarboxylation is conducted at another temperature, the hydrolysis can be conducted for about 12 hours or less. For example, the hydrolysis can be conducted for about 12, 11, 10, 9, 8, 7, 6, 5, 4, 3, 2, or about 1 hour. In these embodiments, the decarboxylation can be conducted for about 24 hours or less. For example, the decarboxylation can be conducted for about 24, 22, 20, 18, 16, 14, 12, 10, or about 8 hours.

Compounds of formula I produced according to the described methods can be isolated and optionally purified using methods known to those of ordinary skill in the art. In other embodiments, compounds of formula I can be used for further reactions without isolation or purification.

Alternatively, compounds of formula I, or stereoisomers thereof, can be prepared from compounds of formula II, or stereoisomers thereof, according to Scheme 2:

Scheme 2

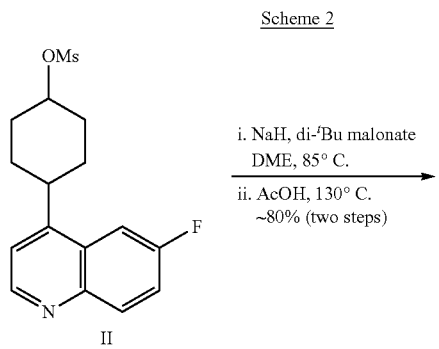

i. NaH, di-<sup>t</sup>Bu malonate
DME, 85° C.

ii. AcOH, 130° C.
~80% (two steps)

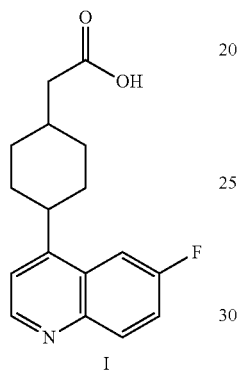

I

In addition to disclosing methods of producing compounds of formula I, and stereoisomers thereof, the disclosure is also directed to methods of producing intermediate compounds, e.g., compounds of formula II, and stereoisomers thereof. Scheme 3 summarizes a method for preparing compounds of formula II, and stereoisomers thereof.

Scheme 3

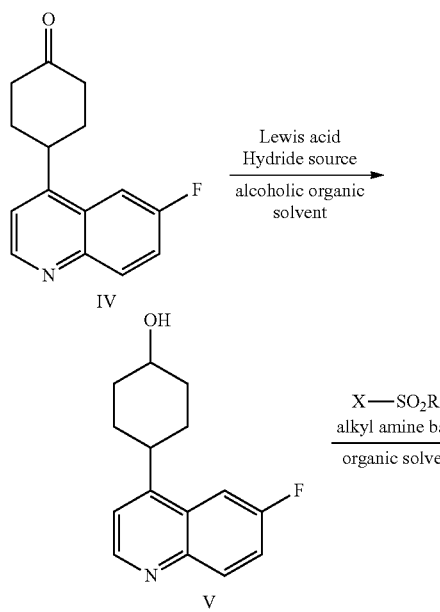

Lewis acid
Hydride source
alcoholic organic solvent

X—SO$_2$R$_1$
alkyl amine base
organic solvent

-continued

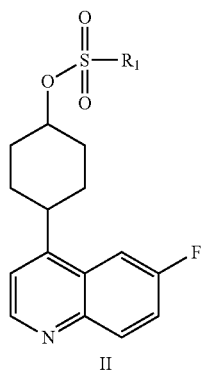

II

Compounds of formula II are prepared by contacting a compound of formula IV:

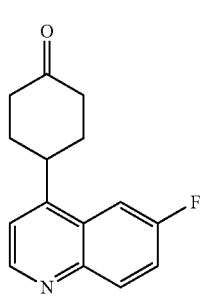

IV with a Lewis acid and a hydride source, in a suitable alcoholic organic solvent, for a time and at a temperature sufficient to reduce the carbonyl and to produce a compound of formula V, or a stereoisomer thereof.

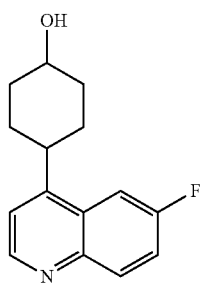

V

The compound of formula V can be a single stereoisomer or a mixture of stereoisomers. For example, the compound of formula V can be provided as a single isomer that is

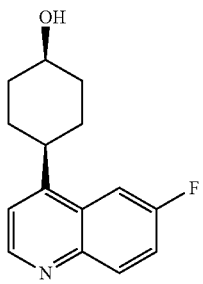

V-A or

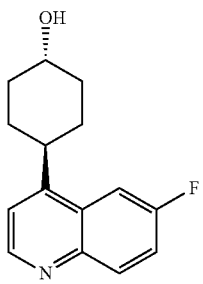

V-B

Alternatively, the compound of formula V can be provided as a mixture of V-A and V-B. In those embodiments employing a mixture of stereoisomers, that is, a mixture of V-A and V-B, the mixture can comprise 99 wt. % of V-B. Alternatively, the mixture can comprise about 95 wt. %, 90 wt. %, 85 wt. %, 80 wt. %, 75 wt. %, 70 wt. %, 65 wt. %, 60 wt. %, 55 wt. %, 50 wt. %, 45 wt. %, 40 wt. %, 35 wt. %, 30 wt. %, 25 wt. %, 20 wt. %, 15 wt. %, 10 wt. %, or about 5 wt. % of V-B.

In some embodiments, the compound of formula IV is provided as a salt of the compound of formula IV. Suitable salts include any salt, for example a hydrochloric, hydrobromic, nitric, carbonic, monohydrogencarbonic, phosphoric, monohydrogenphosphoric, dihydrogenphosphoric, sulfuric, monohydrogensulfuric, hydriodic, phosphorous acids, acetic, propionic, isobutyric, malonic, benzoic, succinic, suberic, fumaric, mandelic, phthalic, benzenesulfonic, p-tolylsulfonic, citric, tartaric, camphorsulfonic, or methanesulfonic acid salt.

In those aspects wherein the compound of formula IV is provided as a salt form, the salt form can be treating with a suitable base (e.g. sodium carbonate, potassium carbonate) to "free base" compound of formula IV. A molar excess of the base is used for the free basing transformation. The free compound of formula IV can be isolated and optionally purified prior to being used in subsequent reactions using techniques known to those of ordinary skill in the art. Alternatively, the free compound of formula IV can be used in subsequent conversions without being isolated.

Lewis acids employed for the conversion of the compounds of formula IV to compounds of formula V are known and include, for example, calcium halides (e.g., $CaCl_2$), lithium halides (e.g., LiBr, LiCl), magnesium halides (e.g., $MgBr_2$), zinc halides (e.g., $ZnCl_2$, $ZnBr_2$), and cerium halides (e.g., $CeBr_3$, $CeCl_3$). Preferred Lewis acids are cerium halides, with $CeCl_3$ (e.g., $CeCl_3$ heptahydrate) being particularly preferred.

Hydride ($H^-$) sources employed for the conversion of the compounds of formula IV to compounds of formula V are known and include, for example, $NaBH_4$, $LiAlH_4$, diisobutylaluminum hydride, and $NaCNBH_4$. $NaBH_4$ is particularly preferred. An alternative hydride source is NaH.

In preferred embodiments, the molar ratio of the Lewis acid, relative to the compound of formula IV is about 0.05:1 to about 0.5:1 or about 0.1:1 to about 0.3:1. For example, the molar ratio of the Lewis acid, relative to the compound of formula IV is about 0.05:1, 0.1:1, 0.15:1, 0.2:1, 0.25:1, 0.3:1, 0.35:1, 0.4:1, 0.45:1, or about 0.5:1.

In preferred embodiments, the molar ratio of the hydride to the compound of formula IV is about 0.5:1 to about 5:1 or about 0.8:1 to about 2:1. For example, the molar ratio of the hydride to the compound of formula IV is about 0.5:1, 0.6:1, 0.7:1, 0.8:1, 0.9:1, 1:1, 1.5:1, 2:1, 2.5:1, 3:1, 3.5:1, 4:1, 4.5:1, or about 5:1.

In preferred embodiments, the molar ratio of the Lewis Acid, relative to the hydride is about 0.01:1 to about 0.5:1 or 0.05:1 to about 0.375:1. For example, the molar ratio of the Lewis Acid, relative to the hydride is about 0.01:1, 0.02:1, 0.03:1, 0.04:1, 0.05:1, 0.06:1, 0.07:1, 0.08:1, 0.09:1, 0.1:1, 0.125:1, 0.15:1, 0.175:1, 0.2:1, 0.225:1, 0.25:1, 0.275:1, 0.3:1, 0.325:1, 0.35:1, 0.375:1, 0.4:1, 0.425:1, 0.45:1, 0.475:1, or about 0.5:1.

In preferred embodiments, the Lewis acid and the compound of formula IV are combined prior to the addition of the hydride source to the reaction mixture.

The solvent employed for the conversion of the compounds of formula IV to compounds of formula V are alcoholic solvents or mixtures of alcoholic solvents. Suitable alcoholic solvents include, for example, methanol, ethanol, isopropanol, and mixtures thereof. The alcoholic solvents used for the conversion of the compounds of formula IV to compounds of formula V can also include non-alcoholic, organic solvents, preferably in amounts that are less than 10 wt. %, based on the total weight of solvent. Suitable organic solvents that may be present in the alcoholic solvent include, for example, ethyl acetate, acetone, tetrahydrofuran, methyl ten-butyl ether, isopropyl acetate, acetonitrile, dimethoxy ethane, and mixtures thereof. In preferred embodiments, the alcoholic solvent will be anhydrous, i.e., will have a KF of 2% or less, preferably 1% or less, preferably 0.05% or less.

The conversion of compounds of formula IV to compounds of formula V is conducted at a temperature sufficient to reduce the carbonyl of the compound of formula IV to produce a compound of formula V. Those of skill in the art will readily be able to ascertain an appropriate temperature, using the methods described herein in combination with the knowledge in the all. Preferred temperatures are those that are below 25° C. In some aspects, the temperature is below about 20° C., more preferably below about 10° C. In some aspects, the temperature is about 0° C. In preferred aspects, the temperature is between about −5° C. and about 5° C. As used herein, the temperature refers to the internal temperature of the reaction mixture.

Those of ordinary skill in the art, using the methods described herein in combination with the knowledge in the art, will be readily able to ascertain an appropriate amount of time for the conversion of compounds of formula IV to compounds of formula V. For example, the conversion can be conducted until the conversion is substantially complete, as determined by HPLC. For example, in some aspects, the time is about 12 hours or less. For example, the time can be about 12, 11, 10, 9, 8, 7, 6, 5, 4, 3, 2, or about 1 hour. Preferably, the time is about 2 hours or less.

The compound of formula V, or a stereoisomer thereof, can be used in further conversions without isolation or purification. In other aspects, the compounds of formula V, or stereoisomers thereof, can be isolated, and optionally purified, using methods known to those of ordinary skill in the art, prior to being used for further conversions.

According to the disclosure, the compound of formula V, or a stereoisomer thereof, is converted to a compound of formula II, or stereoisomer thereof, by contacting the compound of formula V, or a stereoisomer thereof, with X—SO$_2$R$_1$, in the presence of an alkyl amine base, in a suitable anhydrous organic solvent, for a time and at a temperature sufficient for X displacement to produce the compound of formula II, or a stereoisomer thereof.

According to the disclosure, X is halo, preferably Cl or Br, in X—SO$_2$R$_1$. R$_1$ is as previously defined. Preferred X—SO$_2$R$_1$ reagents include, for example, methanesulfonyl chloride.

Also according to the disclosure, the compound of formula V, or a stereoisomer thereof, is converted to a compound of formula II, or stereoisomer thereof, by contacting the compound of formula V, or a stereoisomer thereof, with R$_1$SO$_2$—O—SO$_2$R$_1$, in the presence of an alkyl amine base, in a suitable anhydrous organic solvent, for a time and at a temperature sufficient for —O—SO$_2$R$_1$ displacement to produce the compound of formula II, or a stereoisomer thereof. A preferred R$_1$SO$_2$—O—SO$_2$R$_1$ reagent is methanesulfonic anhydride.

Suitable alkyl amine bases for use in the conversion of compounds of formula V to compounds of formula II include, for example, trimethylamine, N,N-diisopropylethylamine, and the like. Mixtures of alkyl amine bases can also be used.

Suitable anhydrous organic solvents for use in the conversion of a compound of formula V to a compound of formula II will have a KF of less than 2%. Preferably, the KF of the anhydrous organic solvent will be less than 1%, preferably less than 0.5%, more preferably less than 0.05%. The anhydrous organic solvent can be a single solvent or a mixture of solvents. Suitable anhydrous organic solvents include halogenated solvents such as dichloromethane. Other suitable anhydrous organic solvents include aromatic hydrocarbons (e.g. toluene, anisole), acetonitrile and isopropyl acetate. Dichloromethane is a particularly preferred anhydrous organic solvent.

The conversion of compounds of formula V to compounds of formula II is conducted at a temperature sufficient to displace the X moiety of the X—SO$_2$R$_1$ reagent (or the —O—SO$_2$R$_1$ moiety of the R$_1$SO$_2$—O—SO$_2$R$_1$ reagent) to produce a compound of formula II. Those of skill in the art will readily be able to ascertain an appropriate temperature, using the methods described herein in combination with the knowledge in the art. Preferred temperatures are those that are below 25° C. In some aspects, the temperature is below about 20° C., more preferably below about 10° C. In some aspects, the temperature is about 0° C., or less. In preferred aspects, the temperature is between about −10 and about −5° C. As used herein, the temperature refers to the internal temperature of the reaction mixture.

Those of ordinary skill in the an, using the methods described herein in combination with the knowledge in the art, will be readily able to ascertain an appropriate amount of time for the conversion of compounds of formula V to compounds of formula II. For example, the conversion can be conducted until the conversion is substantially complete, as determined by HPLC. For example, in some aspects, the time is about 8 hours or less. For example, the time can be about 8, 7, 6, 5, 4, 3, 2, or about 1 hour. Preferably, the time is about 2 hours or less, more preferably about 1 hour.

The compounds of formula II can be produced as a single isomer, i.e., as a compound of formula II-A or II-B. Alternatively, the compound of formula II can be produced as a mixture of II-A and II-B. In those embodiments producing a mixture of stereoisomers, that is, a mixture of II-A and II-B, the mixture can comprise 99 wt. % of II-B. Alternatively, the mixture can comprise about 95 wt. %, 90 wt. %, 85 wt. %, 80 wt. %, 75 wt. %, 70% W %, 65 wt. %, 60 wt. %, 55 wt. %, 50 wt. %, 45 wt. %, 40 wt. %, 35 wt. %, 30 wt. %, 25 wt. %, 20 wt. %, 15 wt. %, 10 wt. %, or about 5 wt. % of II-B.

The compounds of formula II, or a stereoisomer thereof, can be used in further conversions without isolation. In other aspects, the compounds of formula II, or stereoisomers thereof, can be isolated, and optionally purified, using methods known to those of ordinary skill in the an, prior to being used for further conversions.

Alternatively, compounds of formula II can be prepared from compounds of formula IV according to Scheme 4:

Scheme 4

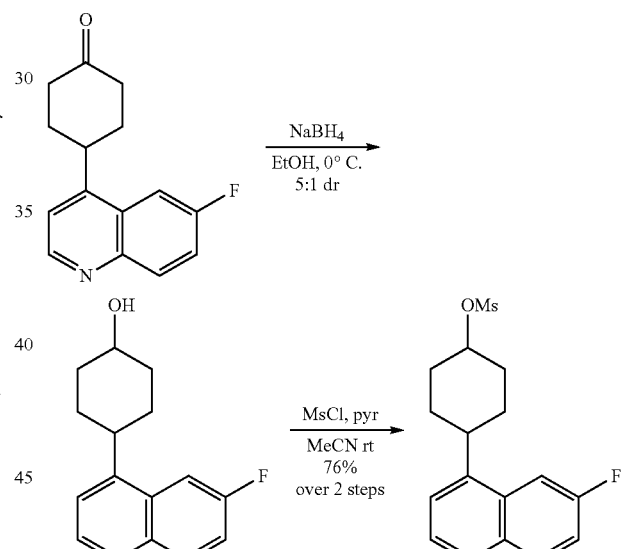

The disclosure is also directed to methods of preparing intermediate compounds of formula IV. Methods to produce compounds of formula IV are depicted in Schemes 5 and 6.

Scheme 5

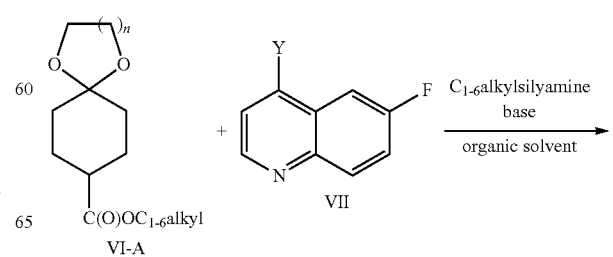

-continued

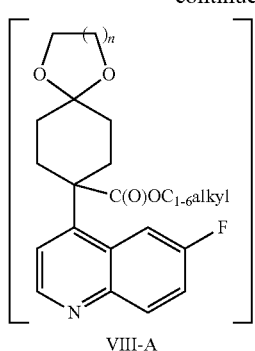

VIII-A

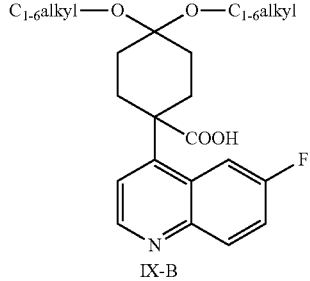

IX-B

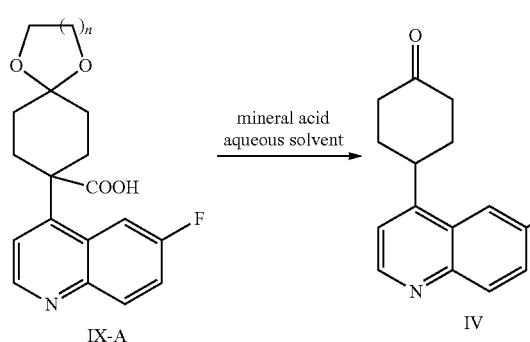

IX-A → IV

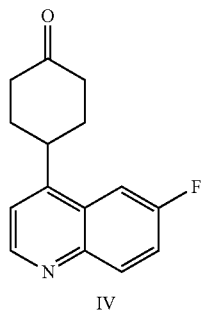

IV

According to those methods, compounds of formula IV are prepared by contacting a compound of formula VI-A or formula VI-B

VI-A

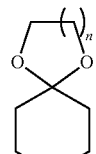

VI-B

Scheme 6

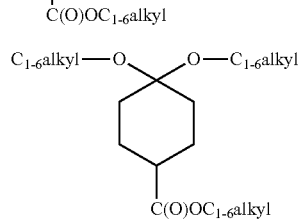

VI-B wherein n is 1 or 2
with a compound of formula VII

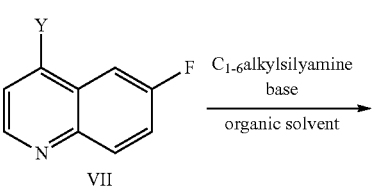

VII

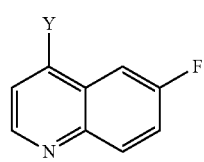

VII

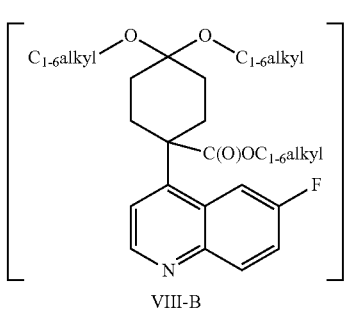

VIII-B herein Y is halo in the presence of a suitable $C_{1-6}$alkylsilyamine base, in a suitable organic solvent, for a time and at a temperature sufficient for Y displacement to produce a compound of formula VIII-A or VIII-B

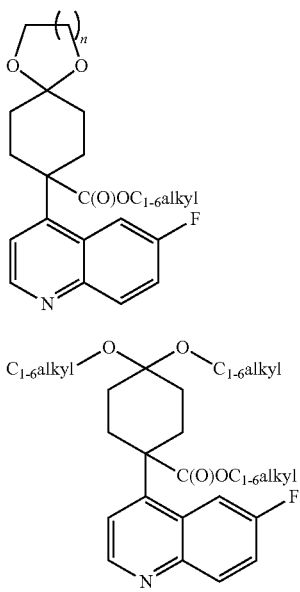

VIII-A

VIII-B

Those of ordinary skill in the art will readily appreciate that compounds and stereoisomers of formula I-C can be produced by substituting the compound of formula VII with a compound of formula VII-A, wherein Y, $R_{10}$, and $R_{11}$ are as previously defined.

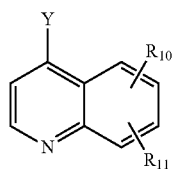

VII-A

Compounds of formula VII-A are known in the art/or can be produced using methods known to those of ordinary skill in the art. See, e.g., WO2016/073770. In preferred aspects, Y is Cl.

Compounds of formula VI-A and VI-B are known and/or can be produced using methods known to those of ordinary skill in the art. According to the disclosure, the $C_{1-6}$alkyl moieties in the compounds of VI-A and VI-B are selected, independently, from $C_{1-6}$alkyl, e.g., methyl, ethyl, propyl, isopropyl, butyl, t-butyl, and the like. In those embodiments employing compounds of formula VI-A, n is preferably 1.

Compounds of formula VII are known in the art/or can be produced using methods known to those of ordinary skill in the art. See, e.g., WO2016/073770. In preferred aspects, Y is Cl.

Preferred embodiments of the conversion of compounds of formula VI-A/VI-B and formula VII to compounds of formula VIII-A/VIII-B employ a molar excess of the compounds of formula VI-A/VI-B to the compounds of formula VII. For example, preferred methods employ a molar ratio of the compounds of formula VI-A/VI-B to the compounds of formula VII of about 1.1:1 to about 2:1 or about 1.5 to about 2:1, e.g., about 1.1:1, 1.2:1, 1.3:1, 1.4:1, 1.5:1, 1.6:1, 1.7:1, 1.8:1, 1.9:1, or about 2:1.

The methods for producing compounds of formula VIII-A or formula VIII-B are conducted in the presence of a suitable $C_{1-6}$silylamine base. An exemplary $C_{1-6}$silylamine base is sodium hexamethyldisilazane (Sodium bis(trimethylsilyl) amide, NaHMDS, $((CH_3)_3Si)_2NNa)$.

In preferred aspects, a molar excess of the $C_{1-6}$silylamine base, relative to the compound of formula VI-A/VI-B is used. For example, preferred methods employ a molar ratio of the $C_{1-6}$silylamine base to the compound of formula VI-A or VI-a of about 1.1:1 to about 5:1, for example, about 1:1, about 2:1, about 3:1, about 4:1 or about 5:1, e.g. about 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5:1, 2.6:1, 2.7:1, 2.8:1, 2.9:1, 3:1, 3.1:1, 3.2:1, 3.3:1, 3.4:1, 3.5:1, 3.6:1, 3.7:1, 3.8:1, 3.9:1, 4:1, 4.2:1, 4.3:1, 4.4:1, 4.5:1, 4.6:1, 4.7:1, 4.8:1, 4.9:1, or about 5:1.

Suitable organic solvents for use in the preparation of compounds of formula VIII-A or formula VIII-B can include a single solvent or a mixture of solvents. Exemplary organic solvents include, for example, toluene, anisole, dimethyl formamide, tetrahydrofuran, and mixtures thereof. Mixtures of toluene and tetrahydrofuran are particularly preferred.

The conversion of compounds of formula VI-A/VI-B and compounds of formula VII to compounds of formula VIII-A or VIII-B is conducted at a temperature sufficient to displace the Y moiety from the compound of formula VII. Those of skill in the art will readily be able to ascertain an appropriate temperature, using the methods described herein in combination with the knowledge in the art. Preferred temperatures are those that are below 25° C. In some aspects, the temperature is below about 20° C., more preferably below about 10° C. In some aspects, the temperature is about 0° C., or less. In preferred aspects, the temperature is less than about −10° C., preferably −20° C., or less. As used herein, the temperature refers to the internal temperature of the reaction mixture.

Those of ordinary skill in the art, using the methods described herein in combination with the knowledge in the art, will be readily able to ascertain an appropriate amount of time for the conversion of compounds of formula VI-A/VI-B and compounds of formula VII to compounds of formula VIII-A or VIII-B. For example, the conversion can be conducted until the conversion is substantially complete, as determined by HPLC. For example, in some aspects, the time is about 8 hours or less. For examples the time can be about 8, 7, 6, 5, 4, 3, 2, or about 1 hour. Preferably, the time is about 4 hours or less, preferably about 3 hours.

The compounds of formula VIII-A and formula VIII-B can be used without isolation or purification in subsequent conversions. Alternatively, the compounds of formula VIII-A and formula VIII-B can be isolated and optionally purified prior to use in subsequent reactions.

According to the disclosure, compounds of formula VIII-A/VIII-B can be used to produce compounds of formula IX-A/IX-B. Compounds of formula IX-A and IX-B can be produced by contacting the compound of formula VIII-A or VIII-B with a suitable hydroxide base, in a suitable aqueous solvent, for a time and at a temperature sufficient for hydrolysis to produce a compound of formula IX-A or formula IX-B

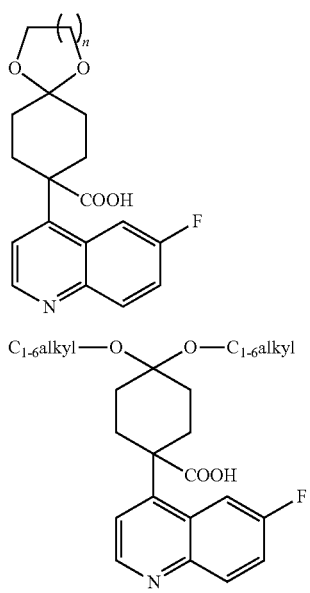

Exemplary hydroxide bases include KOH and NaOH. Mixtures of hydroxide bases can also be used. In exemplary embodiments, the hydroxide base is provided as an aqueous solution, preferably about a 5N or about a 10N aqueous solution.

In preferred embodiments, a molar excess of the hydroxide base, relative to the compound of formula VIII-A/VIII-B is employed. For example, the molar ratio of the hydroxide base to the compound of formula VIII-A/VIII-B is 1:1 to about 50:1 or 5:1 to about 50:1 or about 1:1 to about 10:1, for example, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, or about 50:1.

Suitable aqueous solvents for use for the preparation of compounds of formula IX-A and IX-B include mixtures of water and one or more organic solvents. Suitable organic solvents include ethanol, toluene, anisole, dimethyl formamide, tetrahydrofuran, and mixtures thereof. A particularly preferred aqueous solvent is a mixture is water, tetrahydrofuran, and toluene.

The conversion of compounds of formula VIII-A/VIII-B to compounds of formula IX-A or IX-B is conducted at a temperature sufficient to hydrolyze the compounds of formula VIII-A and VIII-B. Those of skill in the art will readily be able to ascertain an appropriate temperature, using the methods described herein in combination with the knowledge in the art. Preferred temperatures are those that are above 25° C. In some aspects, the temperature is about 50° C., or greater, preferably about 60° C., or greater. As used herein, the temperature refers to the internal temperature of the reaction mixture.

Those of ordinary skill in the art, using the methods described herein in combination with the knowledge in the art, will be readily able to ascertain an appropriate amount of time for the conversion of compounds of formula VIII-A/VIII-B to the compounds of formula IX-A and IX-B. For example, the conversion can be conducted until the conversion is substantially complete, as determined by HPLC. For example, in some aspects, the time is about 24 hours or less. For example, the time can be about 24, 22, 20, 18, 16, 14, 13, 12, 10, 8, 7, 6, 5, 4, 3, 2, or about 1 hour. Preferably, the time is about 20 hours or less, preferably about 10 hours.

Compounds of formula IV can be produced from compounds of formula IX-A or IX-B by contacting the compound of formula IX-A or IX-B with a suitable mineral acid, in a suitable aqueous solvent, for a time and at a temperature sufficient for hydrolysis to produce the compound of formula IV.

Suitable mineral acids that can be used to produce the compounds of formula IV include, for example, HCl, HBr, $H_2SO_4$, $HNO_3$, $H_3PO_4$, and combinations thereof. A preferred mineral acid is HCl.

In preferred embodiments, a molar excess of the mineral acid, relative to the compound of formula IX-A/IX-B is employed. For example, the molar ratio of the mineral acid to the compound of formula IX-A/IX-B is about 5:1 to about 50:1 or about 5:1 to about 7:1, e.g., about 5:1, 6:1, 7:1, 8:1, 9:1, 10:1, 15:1, 20:1, 25:1, 30:1, 35:1, 40:1, 45:1, or about 50:1.

Suitable aqueous solvents for use for the preparation of compounds of formula IV include mixtures of water and one or more organic solvents. Suitable organic solvents include ethanol, toluene, anisole, dimethyl formamide, tetrahydrofuran, and mixtures thereof. A particularly preferred aqueous solvent is a mixture is water, tetrahydrofuran, and toluene.

The conversion of compounds of formula IX-A/IX-B to compounds of formula IV conducted at a temperature sufficient to hydrolyze and decarboxylate the compounds of formula IX-A and IX-B. Those of skill in the art will readily be able to ascertain an appropriate temperature, using the methods described herein in combination with the knowledge in the art. Preferred temperatures are those that are above 25° C. In some aspects, the temperature is about 50° C., or greater, preferably about 60° C., or greater. A preferred temperature range is between about 55° C. and about 65° C. As used herein, the temperature refers to the internal temperature of the reaction mixture.

Those of ordinary skill in the art, using the methods described herein in combination with the knowledge in the art, will be readily able to ascertain an appropriate amount of time for the conversion of compounds of formula IX-A/IX-B to compounds of formula IV. For example, the conversion can be conducted until the conversion is substantially complete, as determined by HPLC. For example, in some aspects, the time is about 24 hours or less. For example, the time can be about 24, 22, 20, 18, 16, 14, 13, 12, 10, 8, 7, 6, 5, 4, 3, 2, or about 1 hour. Preferably, the time is about 20 hours or less, preferably about 10 hours or less, more preferably about 3 hours.

Alternatively, compounds of formula IV can be prepared according to Scheme 7.

Scheme 7

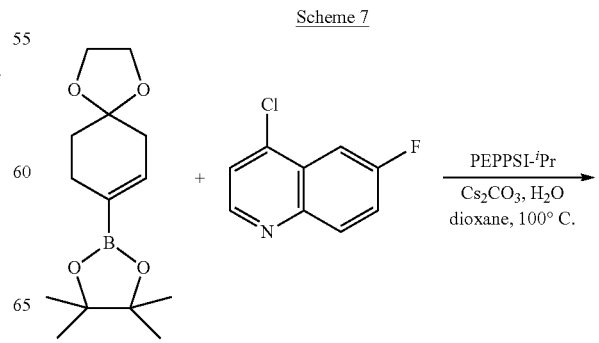

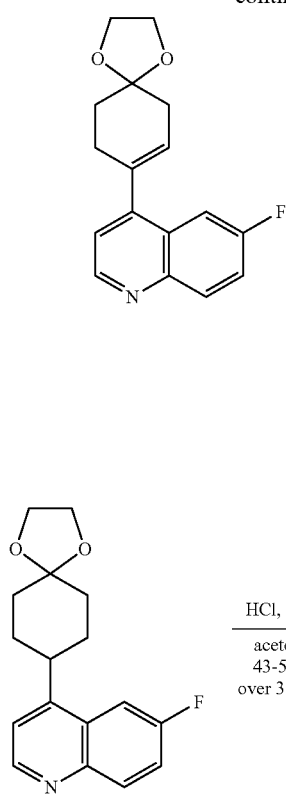

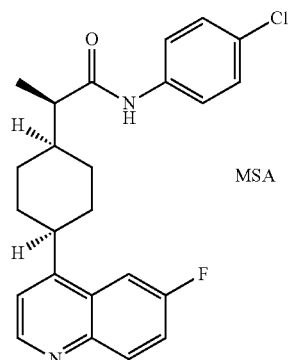

MSA

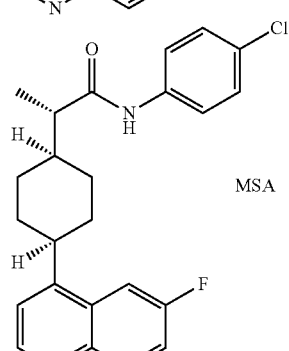

MSA

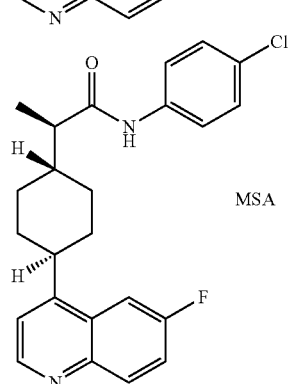

MSA

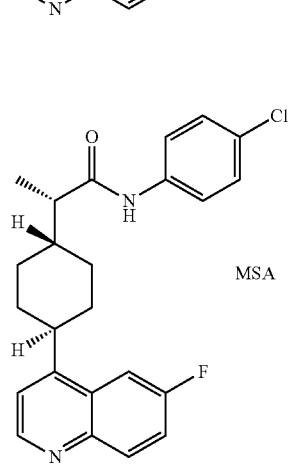

MSA

Compounds of formula IV can be used without isolation or purification in subsequent reactions. Alternatively, compounds of formula IV can be isolated, and optionally purified, using techniques known to those of ordinary skill in the art, prior to being used in subsequent reactions.

Compounds of formula I are useful in the preparation of pharmaceutical compounds, for example, IDO inhibitors. Compound 1, and its stereoisomers, as well as isotopic variants and pharmaceutically acceptable salts and co-crystals, are exemplary embodiments of such IDO inhibitors. Isotopic variants of Compound 1 include those containing one or more $^{13}C$, one or more $^{2}H$, one or more $^{18}F$, one or more $^{15}N$, or a combination thereof.

Compound 1

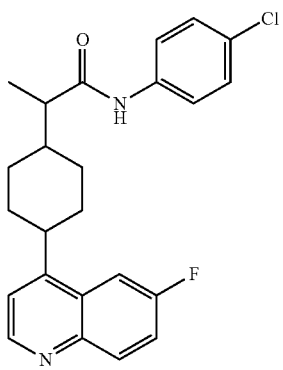

A preferred salt of Compound 1, as well as its stereoisomers, is the Compound 1 methanesulfonic acid salt.

Compounds of formula I be converted to Compound 1, and its stereoisomers, using methods previously described in the art, for example, as described in, e.g., WO2016073770. Alternatively, compounds of formula I, and stereoisomers thereof, can be converted to Compound 1, or a stereoisomer thereof, according to Scheme 8:

Scheme 8
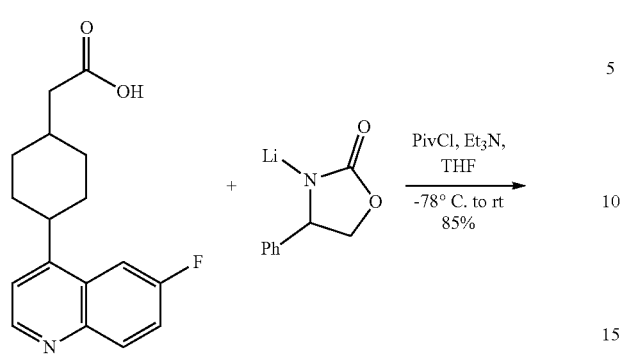
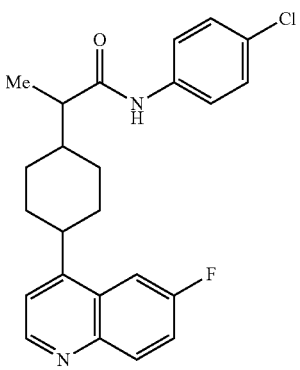
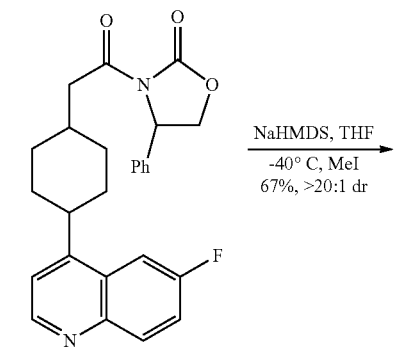
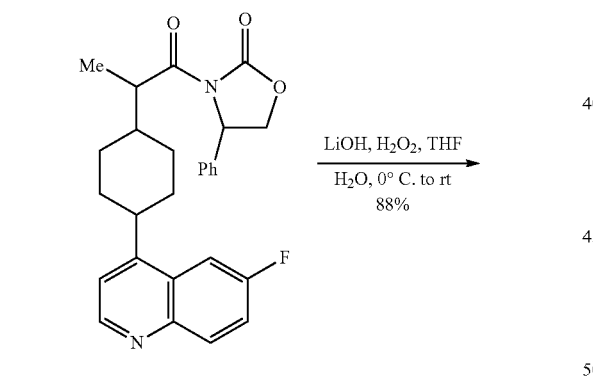
In other aspects, compounds of formula I, and stereoisomers thereof, can be converted to Compound 1, or a stereoisomer thereof, according to Scheme 9:
Scheme 9
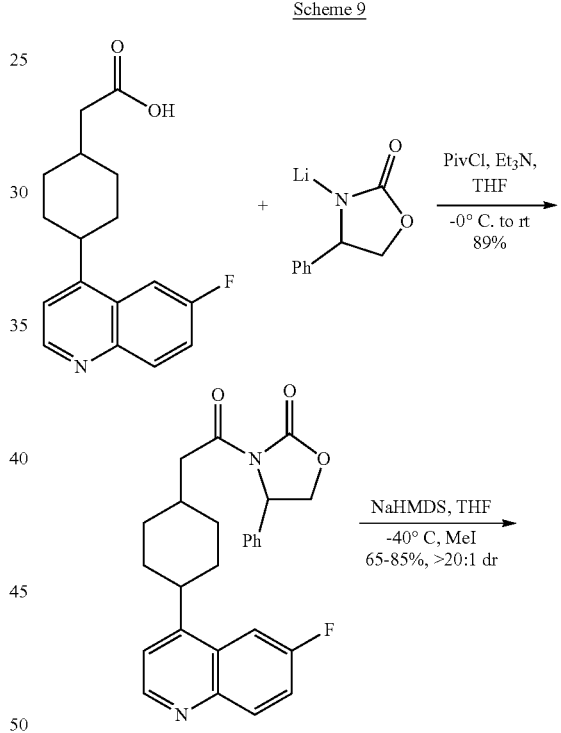
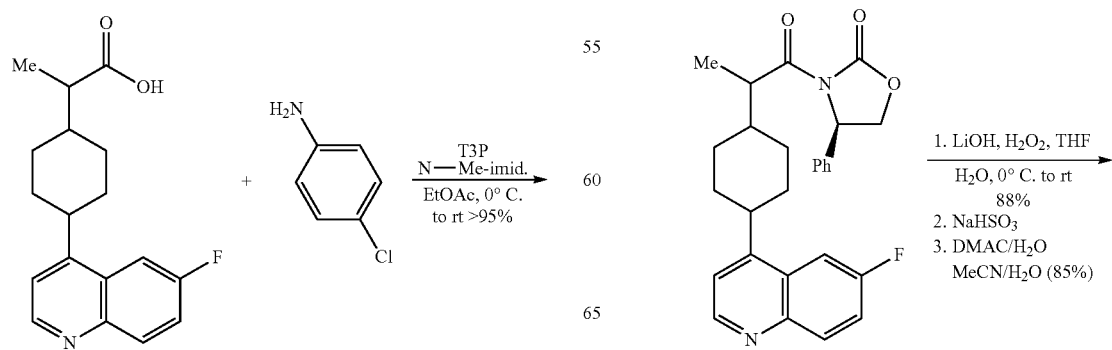

-continued

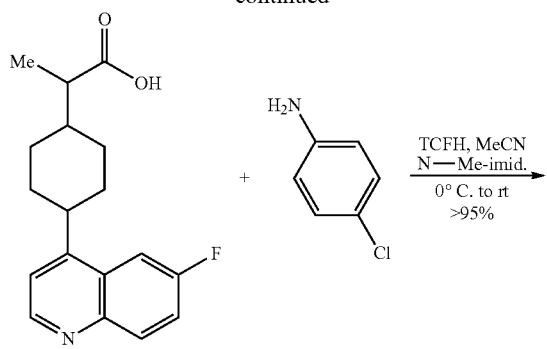

Pharmaceutically acceptable salts and co-crystals of Compound 1 can also be prepared using methods described herein and in the art.

Also within the scope of the discourse are alternative methods for preparing compounds of formula X, and stereoisomers thereof

X

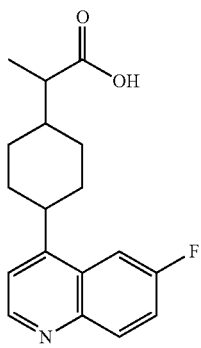

Compounds of formula X can be prepared as single stereoisomers using the methods described herein, in combination with the knowledge of one of ordinary skill in the art:

X-A

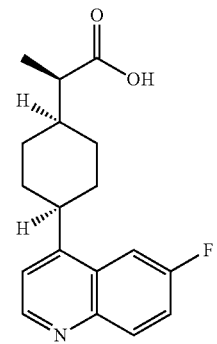

X-B

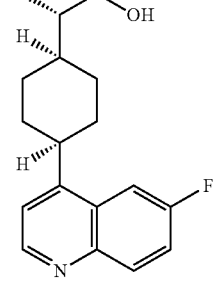

X-C

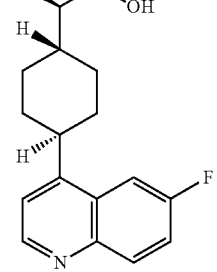

X-D

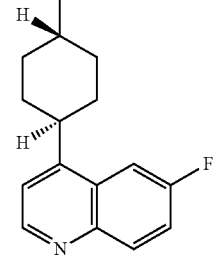

Mixtures of stereoisomers, that is, mixtures of any two of X-A, X-B, X-C, and X-D, in any amount, can also be prepared.

Compounds of formula X, or stereoisomers thereof, can be prepared according to the following Scheme 10

Scheme 10

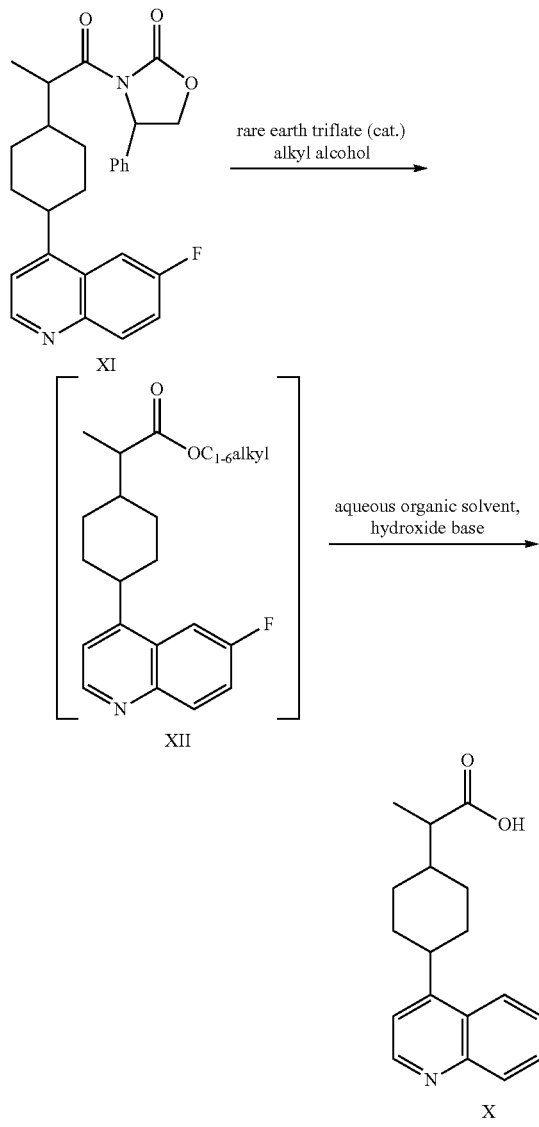

According to the disclosure, a compound of formula XI, or a stereoisomer thereof, is convened to a compound of formula XII, or a stereoisomer thereof, by contacting the compound of formula XI (or stereoisomer thereof) with a rare earth catalyst, for example, a rare earth triflate or a rare earth alkoxide, in the presence of an alkyl alcohol solvent, fora time and at a temperature sufficient to produce the compound of formula XII (or stereoisomer thereof).

Suitable rare earth triflates include, for example, Yb(OTf)$_3$ and Y(OTf)$_3$, as well as mixtures thereof. Preferably, a catalytic amount of the rare earth triflate is used. For example, about 10 mol % of the rare earth vitiate, relative to the compound of formula XI, can be used. Less than 10 mol % can also be used, for example, about 1, 2, 3, 4, 5, 6, 7, 8, or 9 mol %.

Suitable rare earth alkoxides include, for example, Yb(OCH$_3$)$_3$ and Y(OCH$_3$)$_3$, as well as mixtures thereof. Preferably, a catalytic amount of the rare earth alkoxide is used. For example, about 10 mol % of the rare earth alkoxide, relative to the compound of formula XI, can be used. Less than 10 mol % can also be used, for example, about 1, 2, 3, 4, 5, 6, 7, 8, or 9 mol %.

Suitable alkyl alcohol solvents are C$_{1-6}$alkyl alcohols, which include methanol, ethanol, isopropanol, propanol, butanol, and t-butanol, and mixtures thereof. Methanol is particularly preferred as the alkyl alcohol solvent.

The conversion of compounds of formula XI to compounds of formula XII is conducted at a temperature sufficient displace the oxazolidinone moiety. Those of skill in the art will readily be able to ascertain an appropriate temperature, using the methods described herein in combination with the knowledge in the an. Preferred temperatures are those that are ambient temperature, for example, about 25° C. In other embodiments, the temperature is above ambient temperature, for example, at the reflux temperature of the alkyl alcohol solvent. In some aspects, the temperature is about 60° C. As used herein, the temperature refers to the internal temperature of the reaction mixture.

Those of ordinary skill in the art, using the methods described herein in combination with the knowledge in the art, will be readily able to ascertain an appropriate amount of time for the conversion of compounds of formula XI to compounds of formula XII. For example, the conversion can be conducted until the conversion is substantially complete, as determined by HPLC. In some aspects, the amount of time for substantial conversion to formula I is about 10 hours. In other aspects, the amount of time for substantial conversion is about 10 hours or less, for example, about 1, 2, 3, 4, 5, 6, 7, 8, or about 9 hours.

Compounds of formula XII produced according to the described methods can be isolated and/or purified using methods known to those of ordinary skill in the art. In other embodiments, compounds of formula XII can be used for further reactions without isolation and/or purification.

Compounds of formula XII, or stereoisomers thereof, can be converted to compounds of formula X, or stereoisomers thereof, by contacting the compound of formula XII (or stereoisomer thereof) with a hydroxide base, in an aqueous organic solvent, for a time and at a temperature sufficient to produce the compound of formula X, or stereoisomer thereof.

Exemplary hydroxide bases include KOH and NaOH. Mixtures of hydroxide bases can also be used. In exemplary embodiments, the hydroxide base is provided as an aqueous solution, preferably about a 5N or about a 10N aqueous solution.

In preferred embodiments, a molar excess of the hydroxide base, relative to the compound of formula XI is employed. For example, the molar ratio of the hydroxide base to the compound of formula XI is about 5:1 to about 50:1 or about 5:1 to about 10:1, e.g. about 5:1, 6:1, 7:1, 8:1, 9:1, 10:1, 15:1, 20:1, 25:1, 30:1, 35:1, 40:1, 45:1, or about 50:1.

Suitable aqueous solvents for use for the preparation of compounds of formula X include mixtures of water and one or more organic solvents. Suitable organic solvents include ethanol, toluene, anisole, dimethyl formamide, tetrahydrofuran, N,N-dimethylacetamide, and mixtures thereof. A particularly preferred aqueous solvent is a mixture is water and N,N-dimethylacetamide.

The conversion of compounds of formula XII to compounds of formula X is conducted at a temperature sufficient to produce the compound of formula X. Those of skill in the art will readily be able to ascertain an appropriate temperature, using the methods described herein in combination with the knowledge in the art. Preferred temperatures are those that are above 25° C. In some aspects, the temperature is about 30° C. As used herein, the temperature refers to the internal temperature of the reaction mixture.

Those of ordinary skill in the art, using the methods described herein in combination with the knowledge in the art, will be readily able to ascertain an appropriate amount of time for the conversion of compounds of formula XII to the compounds of formula X. For example, the conversion can be conducted until the conversion is substantially complete, as determined by HPLC. For example, in some aspects, the time is about 30 hours or less. For example, the time can be about 30, 28, 26, 24, 22, 20, 18, 16, 14, 13, 12, 10, 8, 7, 6, 5, 4, 3, 2, or about 1 hour. Preferably, the time is about 20 hours or less, preferably about 20 hours.

Compounds of formula X produced according to the described methods can be isolated and optionally purified using methods known to those of ordinary skill in the art. In other embodiments, compounds of formula X can be used for further reactions without isolation or purification.

Compounds described herein can be prepared as either the free compound or as a corresponding salt form, if applicable. Preferred salts include, for example, those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, camphorsulfonic, methanesulfonic, and the like. Camphorsulfonic and methanesulfonic acids are particularly preferred.

In particular, Compound 1, and its stereoisomers, can optionally be converted to a methanesulfonic acid and other suitable pharmaceutically acceptable salts or co-crystals using methods known in the art.

For example, such salts of Compound 1 can be derived from inorganic acids such as hydrochloric, hydrobromic, sulfuric, sulfamic, phosphoric, and nitric; and the salts prepared from organic acids such as acetic, aspartic, propionic, succinic, glycolic, stearic, lactic, malic (e.g., L-malic), tartaric, citric, ascorbic, pamoic, maleic, hydroxymaleic, phenylacetic, glutamic, benzoic, salicylic, sulfanilic, 2-acetoxybenzoic, fumaric, p-toluenesulfonic, ethane sulfonic, ethane disulfonic (e.g., ethane-1,2-disulfonic), oxalic, isethionic, naphthalene-1,5-disulfonic, naphthalene-2-disulfonic, benzenesulfonic, gluconic, hippuric, glutaric, carbonic, isobutyric, malonic, suberic, mandelic, phthalic, camphorsulfonic, and the like.

Also included within the scope of the disclosure are co-crystals Compound 1, formed by combining Compound 1 with a suitable co-crystal former. Exemplary co-crystal formers include amino acids, for example, co-crystals prepared nit proline, glycine, alanine, histidine, arginine, lysine, and the like. Other exemplary co-crystal formers include sugars, for example, monosaccharides such as glucose and fructose. Other co-crystal formers include sugar alcohols such as, for example, mannitol and sorbitol. Amides are other suitable co-crystal formers and include, for example, urea, nicotinamide, and isonicotinamide. Amines are also suitable co-crystal formers and include, for example, imidazole and N-meglumine.

The following Compound 1 stereoisomer is particularly preferred:

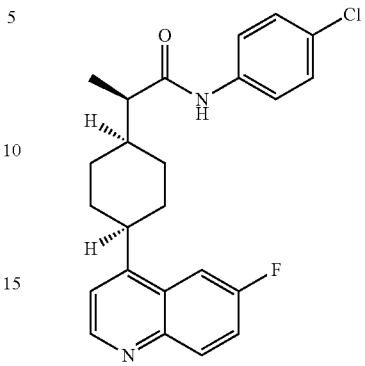

The following Compound 1 stereoisomer methansulfonic acid salt is particularly preferred, due to its advantageous biological, pharmacokinetic, and physicochemical properties:

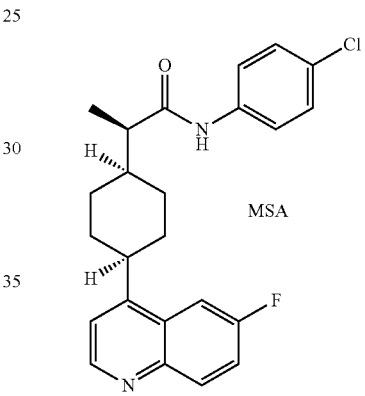

Also within the scope of this disclosure is Compound 1 hydrochloride salt.

Also within the scope of the disclosure is Compound 1 hydrobromide salt.

Also within the scope of the disclosure is Compound 1 nitric acid salt.

Also within the scope of the disclosure is Compound 1 carbonic acid salt.

Also within the scope of the disclosure is Compound 1 monohydrogencarbonic acid salt.

Also within the scope of the disclosure is Compound 1 phosphoric acid salt.

Also within the scope of the disclosure is Compound 1 monohydrogenphosphoric acid salt.

Also within the scope of the disclosure is Compound 1 dihydrogenphosphoric acid salt.

Also within the scope of the disclosure is Compound 1 sulfuric acid salt.

Also within the scope of the disclosure is Compound 1 sulfamic acid salt.

Also within the scope of the disclosure is Compound 1 monohydrogensulfuric acid salt.

Also within the scope of the disclosure is Compound 1 hydroiodic acid salt.

Also within the scope of the disclosure is Compound 1 acetic acid salt.

Also within the scope of the disclosure is Compound 1 aspartic acid salt.
Also within the scope of the disclosure is Compound 1 propionic acid salt.
Also within the scope of the disclosure is Compound 1 isobutyric acid salt.
Also within the scope of the disclosure is Compound 1 malonic acid salt.
Also within the scope of the disclosure is Compound 1 benzoic acid salt.
Also within the scope of the disclosure is Compound 1 succinic acid salt.
Also within the scope of the disclosure is Compound 1 glycolic acid salt.
Also within the scope of the disclosure is Compound 1 stearic acid salt.
Also within the scope of the disclosure is Compound 1 lactic acid salt.
Also within the scope of the disclosure is Compound 1 L-malic acid salt.
Also within the scope of the disclosure is Compound 1 L-tartaric acid salt.
Also within the scope of the disclosure is Compound 1 citric acid salt.
Also within the scope of the disclosure is Compound 1 L-ascorbic acid salt.
Also within the scope of the disclosure is Compound 1 pamoic acid salt.
Also within the scope of the disclosure is Compound 1 maleic acid salt.
Also within the scope of the disclosure is Compound 1 hydroxymaleic acid salt.
Also within the scope of the disclosure is Compound 1 phenylacetic acid salt.
Also within the scope of the disclosure is Compound 1 glutamic acid salt.
Also within the scope of the disclosure is Compound 1 salicylic acid salt.
Also within the scope of the disclosure is Compound 1 sulfanilic acid salt.
Also within the scope of the disclosure is Compound 1 2-acetoxybenzoic acid salt.
Also within the scope of the disclosure is Compound 1 fumaric acid salt.
Also within the scope of the disclosure is Compound 1 p-toluenesulfonic acid salt.
Also within the scope of the disclosure is Compound 1 ethane-1,2-disulfonic acid salt.
Also within the scope of the disclosure is Compound 1 oxalic acid salt.
Also within the scope of the disclosure is Compound 1 isethionic acid salt.
Also within the scope of the disclosure is Compound 1 suberic acid salt.
Also within the scope of the disclosure is Compound 1 mandelic acid salt.
Also within the scope of the disclosure is Compound 1 phthalic acid salt.
Also within the scope of the disclosure is Compound 1 benzenesulfonic acid salt.
Also within the scope of the disclosure is Compound 1 camphorsulfonic acid salt.
Also within the scope of the disclosure is Compound 1 naphthalene-1,5-disulfonic acid salt gluconic acid salt
Also within the scope of the disclosure is Compound 1 hippuric acid salt.
Also within the scope of the disclosure is Compound 1 glutaric acid salt.
Also within the scope of the disclosure is Compound 1 naphthalene-2-disulfonic acid salt.
Also within the scope of the disclosure is Compound 1 proline co-crystal.
Also within the scope of the disclosure is Compound 1 glycine co-crystal.
Also within the scope of the disclosure is Compound 1 alanine co-crystal.
Also within the scope of the disclosure is Compound 1 histidine co-crystal.
Also within the scope of the disclosure is Compound 1 arginine co-crystal.
Also within the scope of the disclosure is Compound 1 lysine co-crystal.
Also within the scope of the disclosure is Compound 1 glucose co-crystal.
Also within the scope of the disclosure is Compound 1 fructose co-crystal.
Also within the scope of the disclosure is Compound 1 mannitol co-crystal.
Also within the scope of the disclosure is Compound 1 sorbitol co-crystal.
Also within the scope of the disclosure is Compound 1 urea co-crystal.
Also within the scope of the disclosure is Compound 1 nicotinamide co-crystal.
Also within the scope of the disclosure is Compound 1 isonicotinamide co-crystal.
Also within the scope of the disclosure is Compound 1 imidazole co-crystal.
Also within the scope of the disclosure is Compound 1 N-meglumine co-crystal.

Compounds of the disclosure that include one or more radioisotopes can be used in imaging. See, e.g., WO2018017529. For example, radiolabeled compounds of the disclosure can be used in Positron Emission Tomography (PET). Such methods are useful in the imaging of cancer in a subject. A preferred radiolabeled compound is

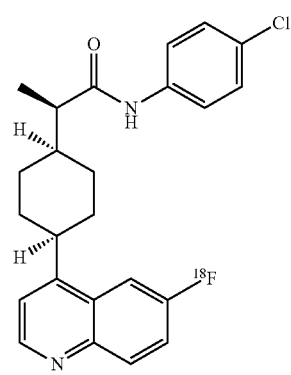

[$^{18}$F]-Compound 1

Pharmaceutically acceptable salts of [$^{18}$F]-Compound 1 are also within the scope of the disclosure. An exemplary method for the preparation of [$^{18}$F]-Compound 1 is depicted in the Scheme below.

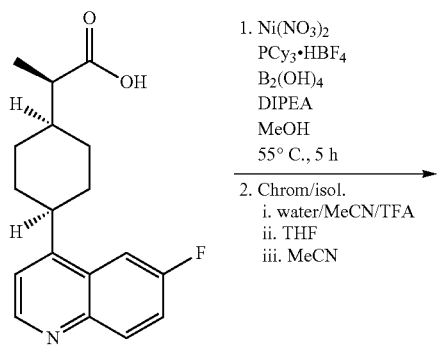

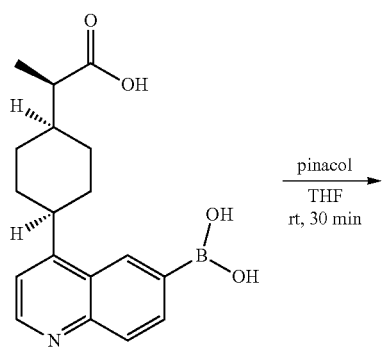

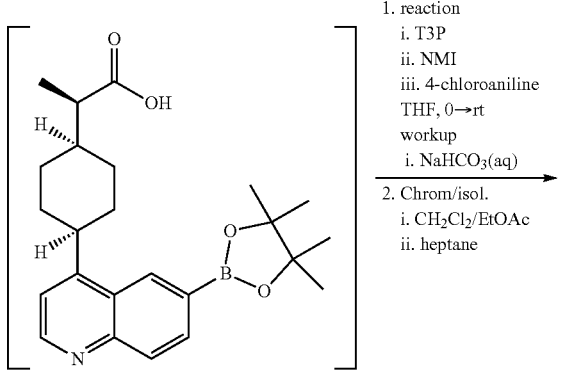

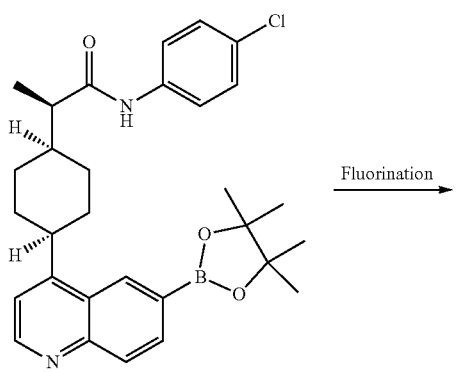

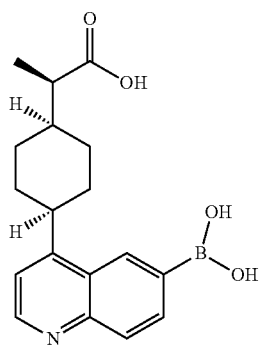 [SMILES: C[C@@H](C(=O)O)[C@H]1CC[C@@H](c2ccnc3ccc(B(O)O)cc32)CC1]

[¹⁸F]-Compound 1

Also within the scope of the disclosure is the following compound, which is a useful intermediate for the preparation of [¹⁸F]-Compound 1.

Exemplary methods and compounds of the disclosure will now be described by reference to their general preparation below and the specific examples that follow. Artisans will recognize that, to obtain the various compounds herein, starting materials may be suitably selected so that the ultimately desired substituents will be carried through the reaction sequence to yield the desired product. Alternatively, it may be necessary or desirable to employ, in the place of the ultimately desired substituent, a suitable group that may be carried through the reaction scheme and replaced as appropriate with the desired substituent.

Compounds of the disclosure can be prepared using the knowledge of one skilled in the art in combination with the present disclosure.

EXAMPLES

Example 1

4-(6-fluoroquinolin-4-yl)cyclohexan-1-one ((1R)-7,7-dimethyl-2-oxobicyclo[2.2.1]heptan-1-yl)methanesulfonate

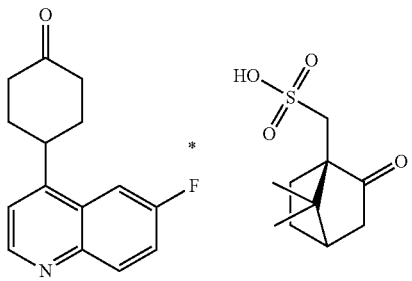 [SMILES: O=C1CCC(c2ccnc3ccc(F)cc23)CC1 ; CC1(C)C2CC[C@]1(CS(=O)(=O)O)C(=O)C2]

A 3000 L reactor (Reactor A) was equipped with mechanical stirrer, a nitrogen inlet and a Dean-Stark apparatus. To the reactor was added 220 kg of ethyl 4-oxocyclohexane-1-carboxylate (1.4 equiv). This was followed by 1463 kg of toluene and 131 kg of ethylene glycol (2.1 equiv). To the mixture 2.2 kg of (1R)-(−)-10-Camphorsulfonic Acid (0.010 equiv) was charged. The batch was heated to reflux (~60-65° C.) under vacuum with Dean Stark trap present. The mixture was held for ~3-4 h until the reaction was completed. To the mixture was charged 402 L of a 5 wt % aqueous solution NaHCO$_3$ (2.4 L, 2.4 L/kg). After agitation for 30 minutes, the phases were allowed to separate and the lower aqueous layer was discarded. To the mixture was charged 402 L of a 5 wt % aqueous solution NaHCO$_3$ (2.4 L, 2.4 L/kg). The organic layer was wash with 403 L of water and the batch was concentrated to 850 L until the KF was <0.02%.

To a 8000 L reactor (reactor B), 168.0 kg of 4-chloro-6-fluoroquinoline, was charged, followed by the toluene solution in reactor A and 790.0 kg of N,N-dimethylformamide which was used to rinse reactor A. Stir until the mixture is homogenous and cool to −20° C. To reactor B was charged 1841 kg of a 1M NaHMDS solution in THF while maintaining the temperature<−20° C. followed by 92 kg of THF. The reaction was held for 3 hours at <−20° C. until complete.

To reactor B was charged 10 L of a 12 w % aqueous ammonium chloride solution maintaining temperature less than 20° C. After agitation for 30 min, the phases were allowed to split and the lower aqueous phase was discarded. To the mixture was charged 840 L of a 12% aqueous solution of sodium chloride. After agitation for 30 min, the phases were allowed to split and the lower aqueous phase was discarded. The aqueous sodium chloride wash was repeated two more times and the organic layer was concentrated under vacuum at 50° C. to 840 L. The mixture was diluted with 541 kg ethanol.

To the mixture was charged 598 kg of 10N potassium hydroxide and the mixture was heated to 60° C. for 10 h until full hydrolysis was achieved. The batch was cooled to 20° C. To a 8000 L reactor (reactor C) was charged 504 kg of water followed by 650 kg of 37 wt % hydrochloric acid. The solution was held at 60° C. and the mixture was transferred from reactor B to reactor C maintaining the temperature between 55-65° C. Carbon dioxide of gassing is observed and is addition controlled. The batch was held at 60-65° C. until reaction reached completion and then was cooled to 35° C.

To the mixture was charge 366 kg of 10N potassium hydroxide over 2 hours maintaining the temperature<45° C. To the mixture was charged 2267 kg of ethyl acetate and 336 kg of water. The batch was cooled to 25° C., the phases were allowed to split and the lower aqueous layer was discarded. To the mixture was charged 504 kg of a 12% aqueous solution of sodium chloride. After agitation for 30 min, the phases were allowed to split and the lower aqueous phase was discarded. The aqueous sodium chloride wash was repeated three more times and the organic layer was concentrated under vacuum at <60° C. to 810 L. The mixture was solvent swapped to ethyl acetate under vacuum at <60° C. and brought to a KF<0.05% and 9 volumes. Solids were removed by polish filtration during transfer to reactor D. Reactor C and the polish filter were rinsed with 360 L of ethyl acetate which was transferred to reactor D. Reactor D was heated to 35° C.

To reactor E was charged 215 kg of (1R)-(−)-10-Camphorsulfonic Acid (1.0 equiv), 2873 kg of ethyl acetate and the mixture was held at 60° C. until homogenous. To reactor E, the contents of reactor D were charged along with 0.8 kg of seeds to effect a crystallization. Reactor D was rinsed into reactor E with 151 kg of ethyl acetate and the slurry was held at 60° C. for 1 hour. The slurry was cooled to 20° C. over the course of 1 hour and held for 8 hours. The solids were filtered and washed twice with 973 kg of ethyl acetate. The solids were dried under vacuum at <50° C. and 340.2 kg of off-white solid was obtained in 73.8% yield.

The following recrystallisation can be performed if desired. To a 2.5 L reactor equipped with a nitrogen inlet and overhead stirrer was charged 50.0 g of 4-(6-fluoroquinolin-4-yl)cyclohexan-1-one ((1R)-7,7-dimethyl-2-oxobicyclo[2.2.1]heptan-1-yl) methanesulfonate followed by 200 mL of acetonitrile. The mixture was heated to 60° C. until a homogenous solution was obtained. The mixture was cooled to 47° C. and 0.20 g of seeds were charged. The slurry was held at 45° C. for 1 hour and 1 L of MTBE was charged over 2 hours between 43-47° C. The slurry was cooled to 20° C. and held for 3 hours. The solids were filtered and washed with 150 mL of 1:5 acetonitrile:MTBE solution followed by 2 washings with 150 mL of MTBE. The solids were dried under vacuum at 50° C. to afford 46.4 g of product in 92.8% yield and 96.0% potency.

$^1$H NMR (400 MHz, DMSO-d$_6$) δ 9.21 (d, J=5.6 Hz, 1H), 8.56 (dd, J=10.5, 2.7 Hz, 1H), 8.36 (dd, J=9.3, 5.3 Hz, 1H), 8.09-7.98 (m, 2H), 6.68-6.58 (m, 4H), 4.17 (m, 1H), 2.96 (d, J=14.7 Hz, 1H), 2.84 (m, 2H), 2.72-2.55 (m, 1H), 2.50-2.46 (m, 1H), 2.42-2.33 (m, 2H), 2.29-2.05 (m, 5H), 2.02-1.79 (m, 3H), 1.38-1.25 (m, 2H), 1.05 (s, 3H), 0.75 (s, 3H); $^{13}$C NMR (101 MHz, DMSO-d$_6$) δ 216.0, 209.4, 162.5, 161.8, 161.8, 160.0, 145.1, 136.0, 128.3, 128.2, 125.9, 125.8, 123.8, 123.5, 119.6, 109.3, 109.1, 58.1, 47.1, 46.9, 42.2, 42.1, 40.3, 36.8, 31.8, 26.3, 24.1, 19.9, 19.5. MS (ESI): calcd for free base C$_{15}$H$_{15}$FNO ([M+H]$^+$), 244.11; found, 244.32. HPLC analysis: Column: Waters XBridge BEH C8 3.5 um, 150×4.6 mm ID; Solvent A: Water:MeCN (95:5 v/v) with 0.05% TFA; Solvent B: Water:MeCN (5:95 v/v) with 0.05% TFA; Gradient: % B: 0 Min. 0%; 22 Min. 50%; 27 Min. 100%; 30 Min. 100%; Stop Time: 30 Min; Flow Rate: 1.2 ml/min; Column temperature: 50° C.; wavelength: 220 nm. The retention time of 4-(6-fluoroquinolin-4-yl)cyclohexan- 1-one ((1R)-7,7-dimethyl-2-oxobicyclo[2.2.1]heptan-1-yl)methanesulfonate was 7.4 min.

Example 1A

A reactor was charged with ethyl 4-oxocyclohexane-1-carboxylate 12 (129 kg, 1.4 equiv), toluene (1122 kg) ethylene glycol (93 kg, 2.1 equiv), and (1R)-(−)-10-Camphorsulfonic Acid (CSA) (1.6 kg, 0.010 equiv). The mixture was heated to reflux (60° C.) under vacuum under Dean-Stark conditions. The mixture was held for 4 h then cooled to 25° C. The organic stream was washed with 5% aqueous solution of NaHCO$_3$ (2×325 kg). The organic layer was washed with water (309 kg) and the organic layer was concentrated to 650 L. The mixture was charged to a solution of 4-chloro-6-fluoroquinoline (129 kg, 1.0 equiv) and DMF (611 kg). The solution was agitated until homogenous and cooled to −20° C. To this solution was charged 40 wt. % NaHMDS solution in THF (719 kg) while maintaining the temperature<−20° C. followed by THF (92 kg). The reaction was held for 3 hours at <−20° C. The mixture was quenched with a 12 wt. % aqueous NH$_4$Cl solution (1417 kg) while maintaining temperature less than 20° C. The mixture was agitated, the phases allowed to split and the lower aqueous layer was discarded. The mixture was washed with a 12 wt. % aqueous NaCl solution (3×662 kg). Ethanol was repeatedly charged and distilled at 550° C. to a volume of 650 L until the THF level was <10.0% and the toluene level was <2.0%, The mixture was diluted with ethanol (424 kg) and a solution of potassium hydroxide (200 kg, 5.0 equiv) and water (258 kg) was charged. The mixture was heated to 55-60° C. for 10-24 h. The batch was then coded to 20° C. A mixture of water (338 kg) and 37 wt % aqueous solution of HCl (519 kg, 7.0 equiv) was heated to 60-65° C. The process stream of product/EtOH was charged to the hot aqueous HCl which results in off-gassing. The reaction was held at 60-65° C. for 3 h during which time further off-gassing was observed. The reaction mixture was cooled to 35° C. and 10 N potassium hydroxide (256 kg) was charged over 2 hours maintaining the temperature<45° C. To the mixture was charged EtOAc (1735 kg). The mixture was cooled to 25° C. the phases were allowed to split and the lower aqueous layer was discarded. The organic layer was washed with a 12% aqueous solution of sodium chloride (4×485 kg). The organic layer was concentrated under vacuum at <60° C. EtOAc was repeatedly charged and distilled at ≤60° C. to a volume of 520 L until the KF was <0.050%, The organic stream was diluted with EtOAc (360 kg). Solids were removed by polish filtration and the filter washed with ethyl acetate (205 kg).

(1R)-(−)-10-Camphorsulfonic Acid (147 kg, 1.0 equiv) and EtOAc (2057 kg) were charged to a separate reactor and heated to 60° C. 45% of the product/EtOAc stream was charged to the (1R)-(−)-10-Camphorsulfonic Acid/EtOAc. Seeds of product (0.6 kg, 0.005 equiv) were charged and the slurry was held at 60° C. for 1 h. The remaining 55% of the product/EtOAc stream was charged over 4 h. The slurry was held 60° C. for 1 h, cooled to 20° C. over 2 h, and held for 8 h. The solids were filtered and washed with EtOAc (2×617 kg). The solids were dried under vacuum at <50° C. affording 340.2 kg of product in 84.8% yield and 98.0 HPLC area percent as an off-white solid. $^1$H NMR (400 MHz, DMSO-d$_6$) δ 9.21 (d, J=5.6 Hz, 1H), 8.56 (dd, J=10.5, 2.7 Hz, 1H), 8.36 (dd, J=9.3, 5.3 Hz, 1H), 8.09-7.98 (m, 2H), 6.68-6.58 (m, 4H), 4.17 (m, 1H), 2.96 (d, J=14.7 Hz, 1H), 2.84 (m, 2H), 2.72-2.55 (m, 1H), 2.50-2.46 (m, 2H), 2.42-2.33 (m, 2H), 2.29-2.05 (m, 5H), 2.02-1.79 (m, 3H), 1.38-1.25 (m, 2H), 1.05 (s, 3H), 0.75 (s, 3H); $^{13}$C NMR (100 MHz, DMSO-d$_6$) δ 216.0, 209.4, 162.5, 161.8, 161.8, 160.0, 145.1, 136.0, 128.3, 128.2, 125.9, 125.8, 123.8, 123.5, 119.6, 109.3, 109.1, 58.1, 47.1, 46.9, 42.2, 42.1, 40.3, 36.8, 31.8, 26.3, 24.1, 19.9, 19.5. HRMS (ESI): calculated for free base C$_{15}$H$_{15}$FNO ([M+H]$^+$), 244.1132; found, 244.1142.

Example 2

(1r,4r)-4-(6-fluoroquinolin-4-yl)cyclohexyl methanesulfonate

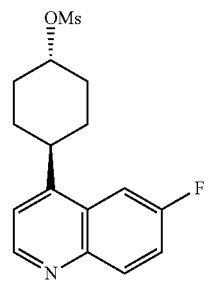 [SMILES: CS(=O)(=O)O[C@H]1CC[C@H](c2ccnc3ccc(F)cc32)CC1]

To an inerted 8000-L glass-lined reactor A was charged 338 kg of 4-(6-fluoroquinolin-4-yl)cyclohexan-1-one ((1R)-7,7-dimethyl-2-oxobicyclo[2.2.1]heptan-1-yl)methanesulfonate (1.0 equiv) and 2275.2 kg of ethyl acetate and a solution of 152.0 kg sodium carbonate (2.0 equiv) in 1690 kg of water. The mixture was agitated for 30 minutes until homogenous. Agitation was stopped, the phases were allowed to split and the lower aqueous layer was discarded. To the organic phase was charged 264.0 kg sodium chloride in 1487 kg water. The mixture was agitated, the phases allowed to split and the lower aqueous layer was discarded. The organic layer was concentrated under vacuum at ≥50° C. to 1250 L. The ethyl acetate was solvent swapped with ethanol until KF was ≤2.0% and residual ethyl acetate was ≤2.0%. The volume was adjusted with ethanol to 1250 L. The mixture was cooled to −5° C.

To an inerted 8000-L glass-lined reactor B was charged 1071.2 kg of ethanol and 54 kg of cerium trichloride heptahydrate. The mixture was held at 25° C. for 1 hour until it was homogenous and then cooled to 5° C. The contents were transferred to reactor A maintaining the temperature<5° C. The transfer was rinsed with 68.7 kg of ethanol. The mixture was cooled to −5° C. and held for 30 minutes. To the mixture 0.08 kg of sodium borohydride (1.0 equiv) was charged in 4 portions, ensuring that the batch temperature did not exceed 0° C. The mixture was held at −5° C. for 1 hour until reaction conversion was completed. To the mixture was charged 213.1 kg citric acid monohydrate in 1879.0 kg of water while maintaining the temperature<20° C., followed by a 68.7 kg ethanol rinse.

The pH was adjusted between pH 4-6 by charging 142.1 kg of sodium bicarbonate in 1626 kg of water was charged while maintaining the temperature at 20° C.

To the solution, 2238 kg of dichloromethane was charged. The mixture was agitated, the phases allowed to split and the lower organic layer was transferred to reactor C. To the solution, 2238 kg of dichloromethane was charged. The mixture was agitated, the phases allowed to split and the lower organic layer was transferred to reactor C.

To reactor C, charge 213.0 kg of citric acid monohydrate in 1879 kg was charged. Then 1420.0 kg of sodium bicarbonate in 1626 kg of water was charged. The mixture was agitated, the phases allowed to split and the lower organic layer was transferred to reactor D. To reactor D, charge 142.1 kg of sodium bicarbonate in 1627 kg of water. The mixture was agitated, the phases allowed to split and the lower organic layer was transferred to reactor E. To reactor E, 169.0 kg of sodium chloride in 1530 kg of water was charged. The mixture was agitated, the phases allowed to split and the lower organic layer was transferred to reactor F. To reactor F 1798.0 kg of dichloromethane was repeatedly charged and distilled at <50° C. to a volume of 1250 L until the KF was <0.05% and residual ethanol was <0.50%, The solution was cooled to 20° C. and 122.4 kg of triethylamine was charged. The mixture was cooled to −5° C. and 98.6 kg methanesulfonyl chloride was charged maintaining the temperature at <0° C. The batch was held at −5° C. for 1 hour until full reaction conversion was achieved. To reactor E, 143.0 kg of ammonium chloride in 1047.0 kg of water was charged maintaining the temperature<20° C. and the mixture was warmed to 20° C. To the mixture was charged 1802 kg of dichloromethane. The mixture was agitated, the phases allowed to split and the lower organic layer was transferred to reactor G. To the mixture was charged 1190.0 kg of water. The mixture was agitated, the phases allowed to split and the lower organic layer was transferred to reactor H. The mixture was distilled under vacuum at <45° C. to 875 L. To this mixture 1800 kg of tetrahydrofuran was charged and the mixture was distilled to 875 L. The distillation and tetrahydrofuran recharge was repeated three times until the KF was <0.05% and the DCM was <0.50%.

The mixture was polish filtered into reactor H, washed with 156.0 kg of THF and distilled under vacuum at <45° C. to a volume of 875 L. The batch is cooled to 20° C. and 0.9 kg of seeds were charged. To the slurry, 1161.0 kg of n-heptane was charged over 6.5 hours. The slurry was held at 20° C. for 3 hours and filtered. The cake was washed with a mixture of 201.1 kg THF: 307.0 kg of n-heptane followed by a 462.0 kg of an n-heptane wash. The cake was dried under vacuum at <50° C. to obtain 156.4 kg in 67.6% yield as an off-white solid.

A recrystallization can be performed. To reactor A was charged 20.13 g of (1r,4r)-4-(6-fluoroquinolin-4-yl)cyclohexyl methanesulfonate and 200 mL of tetrahydrofuran. The mixture was heated to 45° C. and polish filtered into reactor B equipped with an overhead stirrer, thermocouple and nitrogen inlet. The solution was concentrated to 140 mL (7 volumes) at 45° C. and cooled to 20° C. The mixture was seeded and held for 1 hour. 200 mL (10 volumes) of n-heptane was charged over 4 hours and the slurry held overnight. The solids were filtered and washed with 40 mL (2 volumes) of n-heptane. The solids were dried under vacuum at <50° C. to afford 17.73 g in 89.6% yield and 99.38 HPLC area percent.

$^1$H NMR (601 MHz, DMSO-$d_6$) δ 8.80 (d, J=4.5 Hz, 1H), 8.08 (t, J=7.7 Hz, 1H), 8.02 (d, J=10.4 Hz, 1H), 7.65 (m, 1H), 7.40 (d, J=4.7 Hz, 1H), 4.77-4.68 (m, 1H), 3.40-3.30 (m, 1H), 2.19 (m, 2H), 1.95-1.81 (m, 4H), 1.76-1.64 (m, 2H). $^{13}$C NMR (151 MHz, DMSO-$d_6$) δ 160.8, 159.1, 151.1, 149.8, 145.1, 132.6, 127.2, 119.1, 118.9, 118.2, 107.3, 107.1, 80.6, 37.8, 36.0, 32.2, 30.5. MS (ESI): calcd for free base $C_{16}H_{19}FNO_3S$ ([M+H]$^+$), 324.11; found, 324.17. HPLC analysis: Column: Zorbax Eclipse Plus C18 1.8 um, 50×4.6 mm ID: Solvent A: 10 mM NH$_4$OAc with Water:MeCN (90/10 v/v); Solvent B: 10 mM NH$_4$OAc with Water:MeCN (10/90 v/v); Gradient: % B: 0 Min. 0%; 17 Min. 55%; 20 Min. 100%; 24 Min. 100%; Stop Time: 24 Min; Flow Rate: 1.3 ml/min; Column temperature: 25° C.; wavelength: 220 nm. The retention time (1r,4r)-4-(6-fluoroquinolin-4-yl)cyclohexyl methanesulfonate was 12.6 min.

Example 2A

A reactor was charged with 4-(6-fluoroquinolin-4 yl)cyclohexan-1-one ((1R)-7,7-dimethyl-2-oxobicyclo[2.2.1]heptan-1-yl)methanesulfonate (243.6 kg, 1.0 equiv), ethyl acetate (1747 kg), and a 8.3 wt. % aqueous solution of sodium carbonate (1324 kg). The mixture was agitated for 30 minutes until homogenous. Agitation was stopped, the phases were allowed to split and the lower aqueous layer was discarded. The organic stream was washed with 15 wt % aqueous NaCl (1336 kg). Ethanol was repeatedly charged and distilled at ≤50° C. to a volume of 980 L until the KF was <2.0% and residual ethyl acetate was <2.0%.

A separate reactor was charged with cerium (III) trichloride heptahydrate (38.2 kg, 0.20 equiv) and ethanol (771 kg). The mixture was held at 25° C. for 1 hour until it was homogenous, cooled to 5° C., then transferred to the solution of reactant/ethanol. The process stream was cooled to −10° C. Sodium borohydride (19.4 kg) was charged in 4 portions, ensuring that the batch temperature did not exceed 0° C. The mixture was held at −10 to 0° C. for 1 hour. The reaction was quenched with 10 wt % aqueous citric acid (1508 kg) while maintaining the temperature<20° C. The temperature was adjusted to 20° C. and the mixture was agitated for 4 h. The pH was adjusted between pH 4-6 by charging 7.9 wt % aqueous sodium bicarbonate solution (1156 kg). Dichloromethane (1617 kg) was charged. The mixture was agitated for 30 minutes, the phases allowed to split and the upper aqueous layer was transferred to a separate reactor. The aqueous layer was beck-extracted with dichloromethane (1617 kg). The organic layers were combined, and 10 wt % aqueous citric acid (1508 kg) followed by 7.9 wt % aqueous sodium bicarbonate solution (1156 kg) was charged. The mixture was agitated, the phases allowed to split and the upper aqueous layer was discarded. The organic layer was washed with 4.9 wt % aqueous sodium bicarbonate (1276 kg), and further washed with 10 wt % aqueous NaCl (1348 kg).

Dichloromethane was repeatedly charged and distilled at <40° C. to a volume of 980 L until the KF was <0.05% and residual ethanol was <0.50%, The reaction mixture was cooled to 20° C. and triethylamine (88.4 kg, 1.7 equiv) was charged. The mixture was cooled to ° C. and methanesulfonyl chloride (70.5 kg, 1.2 equiv) was charged maintaining the temperature at <0° C. The batch was held at −10 to 0° C. for 1 h. The reaction Was quenched with 12 wt % aqueous ammonium chloride (887 kg) maintaining the temperature<20° C. and the mixture was warmed to 20° C. Dichloromethane (1293 kg) was charged. The mixture was agitated, the phases allowed to split and the upper aqueous layer was discarded. The organic stream was washed with water (850 kg). THF was repeatedly charged and distilled at <45° C. to a volume of 730 L until the KF was <0.05% and dichloromethane was <0.50%

The mixture was polish filtered, washed with THF (434 kg), and distilled under vacuum at <45° C. to a volume of 850 L. The batch is cooled to 20° C. and 0.1 kg of seeds were charged. n-Heptane (835 kg) was charged over 3 h. The slurry was held at 20° C. for 3 h and filtered. The cake was washed with a pre-mixed solution of THF (145 kg) and n-heptane (223 kg) followed by a wash with n-heptane (334 kg). The cake was dried under vacuum at <50° C. to obtain 124.4 kg product in 75.1% yield, 99.0 AP as an off-white solid.

$^1$H NMR (600 MHz, DMSO-d$_6$) δ 8.80 (d, J=4.5 Hz, 1H), 8.08 (t, J=7.7 Hz, 1H), 8.02 (d, J=10.4 Hz, 1H), 7.65 (m, 1H), 7.40 (d, J=4.7 Hz, 1H), 4.77-4.68 (m, 1H), 3.40-3.30 (m, 1H), 2.19 (m, 2H), 1.95-1.81 (m, 4H), 1.76-1.64 (m, 2H). $^{13}$C NMR (150 MHz, DMSO-d$_6$) δ 160.8, 159.1, 151.1, 149.8, 145.1, 132.6, 127.2, 119.1, 118.9, 118.2, 107.3, 107.1, 80.6, 37.8, 36.0, 32.2, 30.5. HRMS (ESI) calculated for C$_{16}$H$_{19}$FNO$_3$S [M+H]$^+$; 324.1064; found, 324.1077.

Example 3

2-((1s,4s)-4-(6-fluoroquinolin-4-yl)cyclohexyl)acetic acid

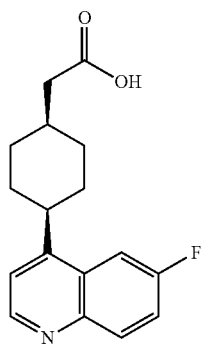 [SMILES: O=C(O)C[C@H]1CC[C@@H](c2ccnc3ccc(F)cc32)CC1]

To an inerted 5000-L glass-lined reactor A was charged 848.8 kg of toluene and 68.6 kg of sodium t-amylate. The mixture was heated to 35° C. and 140.2 kg of di-tert-butyl malonate was charged maintaining the temperature at 35° C. The mixture was stirred for 1 h and 140.0 kg of (1r,4r)-4-(6-fluoroquinolin-4-yl)cyclohexyl methanesulfonate and 364.1 kg of toluene was charged. The mixture was heated to 90° C. and held for 12 hours until full reaction completion was achieved.

The mixture was cooled to 40° C. and 21.0 kg of water and 883.1 kg of sulfolane were charged, followed by 415.9 kg of methanesulfonic acid. The mixture was warmed to 60° C. and held for 1 hour.

The mixture was then heated to 105° C. and held for 14 hours until hill reaction completion was achieved. The mixture was cooled to 60° C. and 560.2 kg of wafer was charged. After cooling to 25° C. 330 kg of potassium hydroxide was charged as an aqueous solution in 407 kg of water. The mixture was held at 25° C. for 1 hour until all solids dissolved, the agitation was halted, the phases were allowed to split and the lower aqueous phase was transferred to an 8000-L glass-lined reactor B. The pH was adjusted to 5.5 using an aqueous acetic acid solution prepared from 144.1 kg of acetic acid and 1226.6 kg of water. The mixture was held for 3 hours and filtered. The wet cake was washed twice with 700 kg of water and twice with 608 kg of toluene. After drying under vacuum at <50° C., 109.2 kg of product was obtained in 87.8% yield) as an off-white solid.

$^1$H NMR (601 MHz, DMSO-d$_6$) δ 12.07 (br s, 1H), 8.79 (d, J=4.3 Hz, 1H), 8.07 (dd, J=9.1, 5.9 Hz, 1H), 7.92 (dd, J=10.8, 2.4 Hz, 1H), 7.63 (td, J=8.6, 2.5 Hz, 1H), 7.48 (d, J=4.5 Hz, 1H), 3.43-3.25 (m, 1H), 2.42 (d, J=7.7 Hz, 2H), 2.34-2.19 (m, 1H), 1.89-1.76 (m, 2H), 1.72-1.60 (m, 6H), 13C NMR (151 MHz, DMSO-d6) δ 174.2, 160.7, 159.1, 152.3, 149.8, 145.1, 132.7, 127.2, 118.6, 107.2, 37.5, 36.2, 29.5, 29.1, 27.4. MS (ESI): calc'd C17H19FNO2 ([M+H]+), 288.14; found, 288.23. HPLC analysis: Column: Zorbax Eclipse Plus C18 1.8 um, 50×4.6 mm ID; Solvent A: 10 mM NH4OAc (pH corrected 7.7) with Water:MeOH (8020 v/v); Solvent B: 10 mM NH4OAc (pH corrected 7.7) with MeOH:Water:MeCN (10/20/70 v/v); Gradient: % B: 0 Min. 14%; 9 Min. 20%; 19 Min. 85%; 20 Min. 85%; 20.5 Min. 100%, Stop Time: 21 Min; Flow Rate: 2.0 ml/min; Column temperature: 45° C.; wavelength: 220 nm. The retention time 2-((1s,4s)-4-(6-fluoroquinolin-4-yl)cyclohexyl)acetic acid was 3.30 min.

Example 3A

A reactor was charged with toluene (1035 kg) and sodium tert-pentoxide (115.2 kg, 1.70 equiv). The mixture was heated to 35° C. and di-tert-butyl malonate (232.9 kg, 1.75 equiv) was charged maintaining the temperature at 35° C. The mixture was stirred for 1 h and (1r, 4r)-4-(6-fluoroquinolin-4-yl)cyclohexyl methanesulfonate (199.0 kg, 1.0 equiv) and toluene (515 kg) was charged. The mixture was heated to 85° C. and held for 12 hours.

The mixture was cooled to 55° C. and water (40 kg) and sulfolane (1255 kg) were charged, followed by methanesulfonic acid (532.2 kg, 9.0 equiv). The mixture was warmed to 60° C. and held for 1 hour. The mixture was then heated to 105° C. and held for 14 hours. The mixture was cooled to 60° C. and water (792 kg) was charged. After cooling to 25° C., aqueous potassium hydroxide (442 kg of KOH and 535 kg of water) was charged. The mixture was held at 25° C. for 1 hour until all solids dissolved, the agitation was halted, the phases ware allowed to split and the lower aqueous phase was transferred to a separate reactor. The pH was adjusted to 5.5 using an aqueous acetic acid solution prepared from 88.7 kg of acetic acid and 1287 kg of water. The mixture was held for 2 hours and filtered. The wet cake was washed with water (2×990 kg) and toluene (2×862 kg). After drying under vacuum at <50° C., 156.9 kg of product was obtained in 88.7% yield, 99.5 HPLC area percent as an off-white solid.

$^1$H NMR (600 MHz, DMSO-d$_6$) δ 12.07 (br s, 1H), 8.79 (d, J=4.3 Hz, 1H), 8.07 (dd, J=9.1, 5.9 Hz, 1H), 7.92 (dd, J=10.8, 2.4 Hz, 1H), 7.63 (td, J=8.6, 2.5 Hz, 1H), 7.48 (d, J=4.5 Hz, 1H), 3.43-3.25 (m, 1H), 2.42 (d, J=7.7 Hz, 2H), 2.34-2.19 (m, 1H), 1.89-1.76 (m, 2H), 1.72-1.60 (m, 6H). $^{13}$C NMR (150 MHz, DMSO-d$_6$) δ 174.2, 160.7, 159.1, 152.3, 149.8, 145.1, 132.7, 127.2, 118.6, 107.2, 37.5, 36.2, 29.5, 29.1, 27.4. HRMS (ESI) calculated for C$_{17}$H$_{19}$FNO$_2$ [M+H]$^+$; 288.1394; found, 288.1406.

Example 4

(R)-3-(2-((1s,4S)-4-(6-fluoroquinolin-4-yl)cyclohexyl)acetyl)-4-phenyloxazolidin-2-one

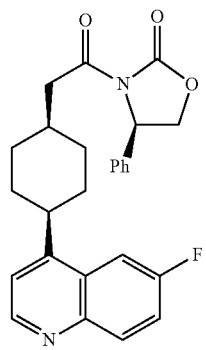 [SMILES: O=C(C[C@H]1CC[C@@H](c2ccnc3ccc(F)cc32)CC1)N1C(=O)OC[C@H]1c1ccccc1]

To an inerted 5000-L glass-lined reactor A was charged THF (1121.7 kg) and 2-(1s,4s)-4-(6-fluoroquinolin-4-yl)cyclohexyl)acetic acid (105.1 kg). Reactor A was rinsed with THF (15.8 kg). The mixture was cooled to −5-5° C. Pivaloyl chloride (64.0 kg) was charged, maintaining temperature −5-5° C. Triethylamine (101.1 kg) was charged maintaining temperature −5-5° C. The mixture was aged at −5-5° C. under the protection of nitrogen for 1 h. (R)-(−)-4-Phenyl-2-oxazolidinone (68.1 kg) was added into the mixture at −5-5° C. Lithium chloride (20.2 kg, ~4.6 kg/lot) was added in four portions at the interval of 10-15 min at −5-5° C. The reactor A wall was rinsed with THF (15.8 kg). The mixture was warmed to 20-25° C. and held for 8 hours until reaction completion was achieved.

Water (1050.6 kg) and isopropyl acetate (825.8 kg) were added into the mixture. The mixture was stirred 1 h. Agitation was stopped, the phases were allowed to split and the lower aqueous layer was discarded. A solution of sodium chloride (105.0 kg) in purified water (948.2 kg) was prepared in a 2000 L glass-lined reactor B. and then the reactor B was transfer into the above organic phase at 20-30° C. The mixture was stirred for 0.5 h. Agitation was stopped, the phases were allowed to split and the lower aqueous layer was discarded. The organic phase was concentrated until 500 L left. Isopropyl acetate (466.3 kg) was added into the mixture. The organic phase was concentrated until 500 L left. Isopropyl acetate (1850.5 kg) was added into the mixture at 45-55° C. and stirred for 0.5-1 h. The organic stream was filtered with a nutsche filter into Reactor B. The filter cake was rinsed with isopropyl acetate (187.0 kg). The combined filtrate was concentrated under reduced pressure until 700 L was left.

The organic stream was heated to 70-75° C. until the solid completely dissolved. The mixture was cooled to 43-47° C. then seeds (0.2 kg) was added into the mixture. The mixture was stirred for 1 h at 43-47° C. n-Heptane (1178.5 kg) was added into the mixture over 3 hours, then aged at 43-47° C. for 1 h. The mixture was cooled to 8-12° C. over 4 hours, and allowed to age for 6 hours. The slurry was filtered with a centrifuge. The solid was rinsed with a solution of isopropyl acetate (45.2 kg) and n-heptane (321.5 kg) through in-line filter. The solids were then rinsed with n-heptane two times (2×358.2 kg). The cake was dried under vacuum at <50° C. to obtain 139.6 kg in 88.2% yield as a white solid.

$^1$H NMR (601 MHz, DMSO-$d_6$) δ 8.80 (d, J=4.5 Hz, 1H), 8.08 (dd, J=9.2, 5.8 Hz, 1H), 7.92 (dd, J=10.9, 2.6 Hz, 1H), 7.63 (td, J=8.7, 2.6 Hz, 1H), 7.43 (d, J=4.5 Hz, 1H), 7.39-7.35 (m, 2H), 7.34-7.27 (m, 3H), 5.50 (dd, J=8.7, 3.8 Hz, 1H), 4.75 (t, J=8.7 Hz, 1H), 4.16 (dd, J=8.7, 3.8 Hz, 1H), 3.34-3.25 (m, 1H), 3.17 (dd, J=15.6, 6.8 Hz, 1H), 3.02 (dd, J=15.7, 8.0 Hz, 1H), 2.35 (br s, 1H), 1.83-1.75 (m, 2H), 1.73-1.56 (m, 6H); $^{13}$C NMR (151 MHz, DMSO-$d_6$) d 171.6, 160.7, 159.1, 153.7, 152.2, 152.1, 149.8, 145.1, 140.0, 132.6, 132.6, 128.7, 127.9, 127.1, 127.1, 125.7, 119.0, 118.8, 118.4, 107.1, 107.0, 69.9, 57.0, 37.4, 36.5, 29.6, 29.0, 28.7, 27.4. MS (ESI): calcd for free base $C_{26}H_{26}FN_2O_3$ ([M+H]$^+$), 433.19; found, 433.19. HPLC analysis: Column: Kinetex C18 100 A 2.6 um, 150×4.6 mm ID; Solvent A: 10 mM NH$_4$OAc with Water:MeCN (95/5 v/v); Solvent B: 10 mM NH4OAc with Water:MeCN (5/95 v/v); Gradient: % B: 0 Min. 15%; 1 Min. 15%; 9 Min. 65%; 12 Min. 65%; 16 Min. 90%; 19.9 Min 100%; 23 Min. 100%; Stop Time: 23 Min; Flow Rate: 1.0 ml/min; Column temperature: 25° C.; wavelength: 220 nm. The retention time (R)-3-(2-((1s,4S)-4-(6-fluoroquinolin-4-yl)cyclohexyl)acetyl)-4-phenyloxazolidin-2-one was 14.0 min.

Example 4A

A reactor was charged with THF (1138 kg) and 2-((1s,4s)-4-(6-fluoroquinolin-4-yl)cyclohexyl)acetic acid (105.1 kg, 1.0 equiv). The mixture was cooled to −5 to 5° C. Pivaloyl chloride (64.0 kg 1.45 equiv) was charged. Triethylamine (101.1 kg, 2.70 equiv) was charged, maintaining temperature −5 to 5° C., then the mixture was aged 1 h. (R)-(−)-4-Phenyl-2-oxazolidinone (68.1 kg, 1.15 equiv) and lithium chloride (20.2 kg, 1.30 equiv) were charged then the reactor wall was rinsed with THF (15.8 kg). The mixture was warmed to 25° C. and held for 8 h.

Water (1050.6 kg) and isopropyl acetate (825.8 kg) were added into the mixture. After mixing for 1 h, the phases were allowed to separate and the bottom aqueous layer was discarded. The organic stream was then washed with 10 wt % aqueous NaCl (1050 kg). The organic stream was concentrated until 500 L left. Isopropyl acetate (466.3 kg) was added, and the organic stream was concentrated until 500 L left. Isopropyl acetate (1850.5 kg) was added into the mixture at 45-55° C. and stirred for 1 h. The organic stream was filtered to remove inorganics and the filter was rinsed with isopropyl acetate (187.0 kg). The combined stream was concentrated under reduced pressure until 700 L was left.

The organic stream was heated to 70-75° C. until the solid completely dissolved. The mixture was cooled to 45° C. then seeds (0.2 kg) were added into the mixture. The mixture was stirred for 1 h. n-Heptane (1178.5 kg) was added into the mixture over 3 hours, then aged at 45° C. for 1 h. The mixture was cooled to 10° C. over 4 hours, and allowed to age for 6 hours. The slurry was filtered with a centrifuge. The solid was rinsed with a pre-mixed solution of isopropyl acetate (45.2 kg) and n-heptane (321.5 kg). The solids were then rinsed with n-heptane (2×358.2 kg). The cake was dried under vacuum at <50° C. to obtain 139.6 kg product in 88.2% yield, 99.95 HPLC area percent as a white solid.

$^1$H NMR (600 MHz, DMSO-$d_6$) δ 8.80 (d, J=4.5 Hz, 1H), 8.08 (dd, J=9.2, 5.8 Hz, 1H), 7.92 (dd, J=10.9, 2.6 Hz, 1H), 7.63 (td, J=8.7, 2.6 Hz, 1H), 7.43 (d, J=4.5 Hz, 1H), 7.39-7.35 (m, 2H), 7.34-7.27 (m, 3H), 5.50 (dd, J=8.7, 3.8 Hz, 1H), 4.75 (t, J=8.7 Hz, 1H), 4.16 (dd, J=8.7, 3.8 Hz, 1H), 3.34-3.25 (m, 1H), 3.17 (dd, J=15.6, 6.8 Hz, 1H), 3.02 (dd, J=15.7, 8.0 Hz, 1H), 2.35 (br s, 1H), 1.83-1.75 (m, 2H), 1.73-1.56 (m, 6H); $^{13}$C NMR (150 MHz, DMSO-$d_6$) d 171.6, 160.7, 159.1, 153.7, 152.2, 152.1, 149.8, 145.1, 140.0, 132.6, 132.6, 128.7, 127.9, 127.1, 127.1, 125.7, 119.0, 118.8, 118.4, 107.1, 107.0, 69.9, 57.0, 37.4, 36.5, 29.6, 29.0, 28.7, 27.4. HRMS (ESI) calculated for $C_{26}H_{26}FN_2O_3$ [M+H]$^+$; 433.1922, found 433.1936.

Example 5

(R)-3-((R)-2-((1s,4S)-4-(6-fluoroquinolin-4-yl)cyclohexyl)propanoyl)-4-phenyloxazolidin-2-one

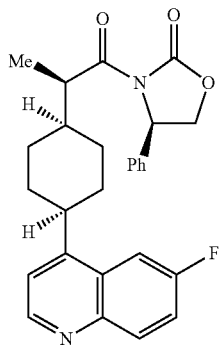

To a 2000-L glass-lined reactor (reactor A) equipped with a nitrogen inlet and condenser was charged 94.96 kg of (R)-3-(2-((1s,4S)-4-(6-fluoroquinolin-4-yl)cyclohexyl)acetyl)-4-phenyloxazolidin-2-one and 838.1 kg of THF. The mixture was heated to 45° C. then 84.6 kg of THF was charged. A 2000 L reactor (reactor B) was charged with 84.7 kg of THF. The mixture in reactor A was transferred through a filter to reactor B and reactor A was rinsed with 41.1 kg of THF into reactor B. The mixture WAS cooled −20° C. and 21.1 kg of THF was charged. To the mixture 50.1 kg of MeI was charged while maintaining the temperature at −20° C. To the mixture was charged 4.8 kg of THF followed by 252.3 kg of 1M sodium bis(trimethylsilyl) amide (NaHMDS) in THF while maintaining the temperature of −20° C. To the mixture was charged 21.0 kg of THF and the mixture was held at −20° C. until the starting material was consumed.

In reactor C, a solution of 16.5 kg of acetic acid in 340.6 kg of THF was prepared and held at −10° C. The contents of reactor B were charged to reactor C while maintaining the temperature in reactor C at <−10° C. Reactor B was rinsed with 21.0 kg of THF into reactor C. The mixture was warmed to 20° C. To 1000-L reactor (reactor D) was charged 65.0 kg sodium chloride and 454.3 kg of water. The contents of reactor C were charged to the sodium chloride solution in reactor D. Alter mixing for 30 minutes, the phases were allowed to separate and the bottom aqueous layer was discharged.

The organic layer was transferred to a 3000 L reactor (reactor E) and distilled to 500 L under vacuum while maintaining the temperature at 50° C. To the mixture was charged 741 kg of acetonitrile and the resulting mixture was distilled down to 500 L. To the mixture was charged 741 kg of acetonitrile and the resulting mixture was distilled down to 500 L. To the mixture 377.7 kg of acetonitrile was charged, the solution was warmed to 60° C., and held at 60° C. for 30 minutes. To the solution was charged 252.2 kg of water over 2.5 hours and temperature was cooled to 52° C. To the solution, 0.95 kg of seeds were charged, the suspension was held for 2 hours and 603.7 kg of water was charged over 3 hours while maintaining the temperature at 52° C. The slurry was cooled to 20° C. over 2.5 hours and held for 4 hours. The slum, was filtered in two portions. Each portion was washed twice with 212 kg of an aqueous acetonitrile solution made from 378.3 kg of acetonitrile and 475.1 kg of water followed by a 237 kg water wash and a 162 kg n-heptane wash. The cakes were combined and dried at 55° C. to afford 80.9 kg of an off-white solid in 83% yield.

A recrystallization can be performed in which 80.9 kg of (R)-3-((R)-2-((1s,4S) 4-(6-fluoroquinolin-4-yl)cyclohexyl)propanoyl)-4-phenyloxazolidin-2-one was charged to a reactor followed by 572.3 kg acetonitrile. The mixture was heated to 60° C. until a homogenous mixture formed. The solution was held at 60° C. for 30 minutes. To the solution was charged 214.4 kg of water over 2.5 hours and temperature was cooled to 52° C. To the solution, 0.81 kg of seeds were charged, the suspension was held for 2 hours and 513.7 kg of water was charged over 3 hours while maintaining the temperature at 52° C. The slurry was cooled to 20° C. over 2.5 hours and held for 4 hours. The slurry was filtered and washed twice with an aqueous acetonitrile solution made from 159.0 kg of acetonitrile and 202.3 kg of water followed by a 404.5 kg water wash and a 276.7 kg n-heptane wash.

$^1$H NMR (601 MHz, DMSO-$d_6$) δ 8.85 (d, J=4.5 Hz, 1H), 8.10 (dd, J=9.2, 5.8 Hz, 1H), 7.97 (dd, J=10.9, 2.6 Hz, 1H), 7.66 (dd, J=8.7, 2.6 Hz, 1H), 7.41-7.40 (m, 3H), 7.32-7.30 (m, 3H), 5.53 (dd, J=8.7, 3.8 Hz, 1H), 4.76 (t, J=8.7 Hz, 1H), 4.29 (m, 1H), 4.15 (dd, J=8.6, 4.2 Hz, 1H), 3.42-3.38 (m, 1H), 2.05-2.01 (dd, 1H), 1.83-1.58 (m, 1H), 1.05 (d, J=8.7 Hz, 3H); $^{13}$C NMR (151 MHz, CDCl$_3$-d) δ 172.1, 161.7, 153.8, 152.1, 149.7, 145.5, 139.1, 132.9, 132.8, 129.2, 128.8, 125.9, 119.1, 118.8, 118.3, 106.7, 106.5, 69.9, 57.7, 38.5, 37.3, 30.3, 29.8, 29.2, 27.9, 27.8; MS (ESI): calcd for $C_{27}H_{28}FN_2O_3$ ([M+H]$^+$), 447.51; found, 447.40.

HPLC analysis: Column: Supelco Ascentis Express C8 2.7 um, 150×4.6 mm PN=USZB002789; Solvent A: 10 mM ammonium acetate in 80% eater and 20% MeOH; Solvent B: 10 mM ammonium acetate in 75% acetonitrile and 20% MeOH and 5% water; Gradient: % B: 0 Min. 10%; 2 Min. 10%; 7 Min. 55%; 20 Min. 68%; 24 Min. 100%; 26 Min. 0% Stop Time: 30 min; Flow Rate: 1 ml/min; wavelength; 218 nm; oven temperature: 30° C. The retention time of (R)-3-((R)-2-((1s,4S)-4-(6-fluoroquinolin-4-yl)cyclohexyl)propanoyl)-4-phenyloxazolidin-2-one was 16.4 min.

Example 5A

A reactor was charged with (R)-3-(2-((1s,4S)-4-(6-fluoroquinolin-4-yl)cyclohexyl)acetyl)-4-phenyloxazolidin-2-one (95.0 kg, 1.0 equiv) and THF (838.1 kg). The mixture was heated to 45° C. then THF (85 kg) was charged. The organic stream was transferred through a filter to another reactor and the filter was rinsed with THF (41.1 kg). The mixture was cooled −20° C. and THF (21 kg) was charged. Methyl iodide (50.1 kg, 1.60 equiv) and 1 M sodium bis(trimethylsilyl) amide (NaHMDS) in THF (252.3 kg, 1.25 equiv) were charged while maintaining the temperature at −20° C. The reactor was rinsed with THF (25.8 kg), then the organic stream was held at −20° C. for 3 h. The reaction was quenched by the addition of 4.6 wt % aqueous acetic acid solution (357 kg) while maintaining the temperature at less than −10° C. The organic stream was warmed to 25° C. and 12.5 wt % aqueous NaCl (519 kg) was charged. After mixing for 30 minutes, the phases were allowed to separate and the bottom aqueous layer was discarded. The organic layer was concentrated to 500 L. Acetonitrile (2×741 kg) was charged and the resulting mixture was twice distilled down to 500 L. Acetonitrile (378 kg) was charged and the solution was warmed to 60° C. and held at that temperature for 30 minutes. Water (252 kg) was charged over 2.5 h and temperature was cooled to 52° C. Seeds (1.0 kg) were charged, the slurry was held for 2 h and water (604 kg) was charged over 3 h while maintaining the temperature at 52° C. The slurry was cooled to 20° C. over 2.5 h and held for 4 h. The slum was filtered then washed twice (2×424 kg) with a pro-mixed solution of acetonitrile (378 kg) and water (475 kg), followed washing with water (237 kg) wash and n-heptane (162 kg). The cake was dried at 55° C. to afford 80.9 kg of product 83% yield, 99.94 HPLC area percent as an off-white solid.

$^1$H NMR (600 MHz, DMSO-$d_6$) δ 8.85 (d, J=4.5 Hz, 1H), 8.10 (dd, J=9.2, 5.8 Hz, 1H), 7.97 (dd, J=10.9, 2.6 Hz, 1H), 7.66 (dd, J=8.7, 2.6 Hz, 1H), 7.41-7.40 (m, 3H), 7.32-7.30 (m, 3H), 5.53 (dd, J=8.7, 3.8 Hz, 1H), 4.76 (t, J=8.7 Hz, 1H), 4.29 (m, 1H), 4.15 (dd, J=8.6, 4.2 Hz, 1H), 3.42-3.38 (m, 1H), 2.05-2.01 (dd, 1H), 1.83-1.58 (m, 1H), 1.05 (d, J=8.7 Hz, 3H); $^{13}$C NMR (150 MHz, DMSO-$d_6$) δ 175.9, 160.7, 159.1, 153.6, 152.3, 152.3, 149.8, 145.2, 139.9, 132.7, 132.6, 128.8, 127.9, 127.2, 127.1, 125.5, 119.0, 118.9, 118.3, 107.2, 107.0, 68.8, 57.0, 37.1, 36.0, 34.7, 28.4, 27.9, 27.5, 26.1, 15.8; HRMS (ESI): calculated for $C_{27}H_{28}FN_2O_3$ [M+H]$^+$; 447.2079, found 447.2091.

Example 6

(R)-2-((1s,4S)-4-(6-fluoroquinolin-4-yl)cyclohexyl) propanoic acid

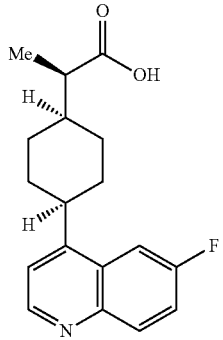

To a 1800-L glass-lined reactor (1) under a nitrogen sweep was charged 254.1 kg of THF and 57.0 kg of (R)-3-((R)-2-((1s,4S)-4-(6-fluoroquinolin-4-yl)cyclohexyl) propanoyl)-4-phenyloxazolidin-2-one followed by 127.0 kg of THF. To the mixture was charged 66.9 kg of a 30% (w/w) solution of hydrogen peroxide (4.6 eq) in water followed by 2.0 kg of water. The mixture was heated to 25° C. and a solution of 8.7 kg LiOH monohydrate in 57.3 kg of water was charged over 4 hours while maintaining the temperature at 25° C. and the oxygen content at <2.5%. To the reactor was charged 9.9 kg of water and 152.4 kg of THF. The reaction was held until full conversion was achieved.

The mixture was cooled to 5° C. and 73.2 kg of sodium bisulfite in 171.8 kg of water was charged slowly while maintaining the temperature at <30° C. The mixture was held for 30 minutes with agitation, then held for 30 minutes without agitation. The phases were split and the bottom aqueous layer was discarded. To the mixture was charged 161.0 kg of N,N-dimethylacetamide (DMAC) and 48.9 kg of THF, followed by vacuum distillation to 130 mbar until a temperature of 70° C. was obtained. To the mixture 26.8 kg of DMAC was added at 70° C. followed by 154.6 kg of water added over 30 minutes. The batch was held at 70° C. for 1.5 hours and 103.0 kg of water was added over 30 minutes. The batch was held at 70° C. for 1.5 hours. The mixture was cooled to 20° C. over 6 hours and held for 60 hours. The slurry was filtered and washed with twice with 167 kg of 1:1 DMA:Water. The cake was washed two times with 162 kg of 1:3 acetonitrile:water and dried at 50° C. under vacuum to afford 35.0 kg of white solid in 91.1% yield. $^1$H NMR (400 MHz, DMSO-$d_6$) δ 12.95 (br s, 1H), 8.80 (d, 1H), 8.08 (dd, 1H), 7.95 (dd, 1H), 7.65 (t, 1H), 7.50 (d, 1H), 3.38 (br 1H), 2.78-2.66 (m, 1H), 1.86-1.61 (m, 9H), 1.09 (d, 3H); $^{13}$C NMR (151 MHz, DMSO-$d_6$) δ 177.7, 159.9 (d, 1C), 152.2 (d, 1C), 149.8 (d, 1C), 145.1, 132.6 (d, 1C), 127.2 (d, 1C), 118.9 (d, 1C), 118.7, 107.1 (d, 1C), 39.1, 37.2, 35.7, 28.7, 27.8, 27.2, 26.2, 15.6; LCMS ESI (+) m/z 302 (M+H).

HPLC analysis: Column: Ascentis Express C18 2.7 um, 150×4.6 mm ID; Solvent A: 0.05% TFA in water:acetonitrile (95:5); Solvent B: 0.05% TFA in water:acetonitrile (5:95); Gradient: % B: 0 Min. 15%; 12 Min. 60%; 14 Min. 100%; 16 Min. 100%; Stop Time: 16 min; Flow Rate: 1 ml/min; wavelength; 218 nm. The retention time of (R)-2-((1s,4S)-4-(6-fluoroquinolin-4-yl)cyclohexyl)propanoic acid was 7.0 min.

Example 6A

A reactor was charged with THF (640 kg) and (R)-3-((R)-2-((1s,4S)-4-(6-fluoroquinolin-4-yl)cyclohexyl)propanoyl)-4-phenyloxazolidin-2-one (144 kg, 1.0 equiv) followed by THF (320 kg). The reactor was charged with 35 wt % aqueous solution of hydrogen peroxide (144 kg, 4.6 equiv) followed by water (14 kg). The mixture was heated to 25° C. and a nitrogen sweep was established to control oxygen of gassing during the LiOH solution charge. A solution of LiOH anhydrous (12.4 kg, 1.6 equiv) in water (144 kg) was charged over 6 h in two portions of 3 h each while maintaining the temperature at 25° C. and the oxygen content at <2.5% in the reactor headspace After the first portion of LiOH solution, THF was charged (128 kg). After the second LiOH solution portion, the reactor was charged with water (14 kg) and THF (128 kg). The reaction was held for 3 h.

The mixture was cooled to 10° C. and a 30 wt % aqueous solution of sodium bisulfate (601 kg) was charged slowly while maintaining the temperature at <35° C. After mixing for 30 minutes, the phases were allowed to separate and the bottom aqueous layer was discarded. The mixture was charged with N,N-dimethylacetamide (DMAc) (541 kg). The mixture was stirred for 1 h at 25° C. and then polish filtered into the distillation vessel. After rinsing through the polish filter with THF (128 kg) and transferring into the distillation vessel, the batch was vacuum distilled at 130 mbar until a temperature of 70° C. was obtained. The reactor was charged with DMAc (68 kg) at 70° C., then water (389 kg) was added over 30 minutes. The batch was held at 70° C. for 1.5 h, then additional water (158 kg) was added over 2 h. The batch was held at 70° C. for 1.5 h. The mixture was cooled to 20° C. over 6 h and held for at least 8 h. The slurry was filtered and washed with a pre-mixed solution of DMAc (203 kg) and water (216 kg). The solids were further washed with a pre-mixed solution of acetonitrile (171 kg) and water (648 kg). The solids were dried at 50° C. under vacuum to afford 86.5 kg of product in 89% yield. 99.7 HPLC area percent as a white solid.

$^1$H NMR (600 MHz, DMSO-$d_6$) δ 12.09 (s, 1H), 8.80 (d, J=4.5 Hz, 1H), 8.06 (dd, J=9.2, 5.8 Hz, 1H), 7.91 (dd, J=10.9, 2.8 Hz, 1H), 7.61 (ddd, J=9.1, 8.2, 2.8 Hz, 1H), 7.45 (d, J=4.5 Hz, 1H), 3.41-3.27 (m, 1H), 2.72-2.63 (m, 1H), 1.86-1.61 (m, 9H), 1.08 (d, J=6.8 Hz, 3H); $^{13}$C NMR (150

MHz, DMSO-$d_6$) δ 177.7, 159.9, 152.2, 149.8, 145.1, 132.6, 127.2, 118.9, 118.7, 107.1, 39.1, 37.2, 35.7, 28.7, 27.8, 27.2, 26.2, 15.6; HRMS (ESI) calculated for $C_{18}H_{21}FNO_2$ [M+H]$^+$; 302.1551, found 302.1563.

Example 7

(R)—N-(4-chlorophenyl)-2-((1s,4S)-4-(6-fluoroquinolin-4-yl)cyclohexyl)propanamide

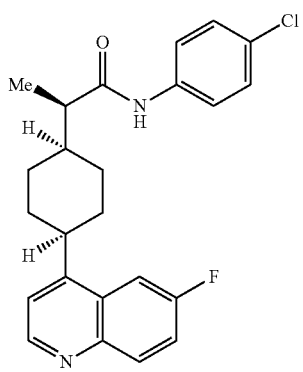 [SMILES: C[C@@H](C(=O)Nc1ccc(Cl)cc1)[C@H]1CC[C@@H](c2ccnc3ccc(F)cc32)CC1]

To a 50 L glass-lined reactor under a blanket of nitrogen was charged 13.75 kg acetonitrile, then 2.68 Kg N,N,N',N'-tetramethylchloroformamidinium hexafluorophosphate (TCFH) and rinsed with 2.0 Kg acetonitrile. 2.03 Kg N-methylimidazole was added followed by 1.95 Kg acetonitrile. 2.48 Kg (R)-2-((1s,4S)-4-(6-fluoroquinolin-4-yl)cyclohexyl)propanoic acid was added followed by 1.05 Kg acetonitrile. The mixture was held for 0.5 h then 1.21 Kg 4-chloroaniline charged followed by 1.0 Kg acetonitrile. The mixture was maintained at 20° C. until the reaction was deemed complete by HPLC analysis. The solution was then heated to 60° C., and 9.25 Kg water was charged. The solution was then cooled to 40° C. the mixture was aged for 1 h. seeds (32 g) were charged and rinsed with 1.15 Kg 2:1 water:acetonitrile, and the resulting slurry was maintained for 1 h. The slurry was then cooled to 20° C. and 25.75 Kg water was charged. The slurry was filtered and the cake was washed three times with 6.9 Kg of 2:1 water:acetonitrile. The cake was dried under vacuum at 50° C. to yield 3.33 Kg of (R)—N-(4-chlorophenyl)-2-((1s,4S)-4-(6-fluoroquinolin-4-yl)cyclohexyl)propanamide hydrate as a white solid in 94.1% yield.

$^1$H NMR (600 MHz, DMSO-$d_6$) δ 10.09 (s, 1H), 8.86 (d, J=4.5 Hz, 1H), 8.08 (dd, J=9.0, 5.6 Hz, 1H), 7.95 (dd, J=10.9, 2.6 Hz, 1H), 7.70-7.60 (m, 3H), 7.54 (d, J=4.5 Hz, 1H), 7.33 (d, J=9.0 Hz, 2H), 3.43-3.31 (m, 3H), 2.90-2.80 (m, 1H), 1.99-1.55 (m, 9H), 1.13 (d, J=6.8 Hz, 3H); $^{13}$C NMR (151 MHz, DMSO-$d_6$) δ 175.0, 159.9, 152.4, 149.7, 145.2, 138.1, 132.7, 128.5, 127.2, 126.7, 120.8, 119.0, 118.6, 107.2, 40.2, 37.4, 35.6, 28.5, 27.6, 27.4, 26.3, 16.1; HRMS (ESI); calcd for $C_{24}H_{24}ClFN_2O$ ([M+H]$^+$), 411.1619; found 411.1649.

Example 7A

A reactor was charged with N,N,N',N'-tetramethylchloroformamidinium hexafluorophosphate (TCFH) (95 kg, 1.25 equiv) and acetonitrile (237 kg). N-Methylimidazole (69 kg, 3.10 equiv) was added followed by acetonitrile (32 kg). (R)-2-((1s,4S)-4-(6-fluoroquinolin-4-yl)cyclohexyl)propanoic acid (82.0 kg, 1.0 equiv) was added followed by acetonitrile (63 kg). The mixture was held for 0.5 h then a solution of 4-chloroaniline (40 kg, 1.15 equiv) dissolved in acetonitrile (96 kg) was charged followed by acetonitrile (63 kg). The mixture was maintained at 20° C. for 3 h, then acetonitrile (128 kg) was added. The solution was then heated to 60° C. and water (303 kg) was charged. The solution was cooled to 40° C., seeds (0.8 kg) were charged, and the resulting slurry was maintained for 1 h. The slurry was cooled to 20° C. over 3 h. Water (820 kg) was charged over 1.5 h and the slurry was aged for 1 h. The slurry was filtered and the cake was washed three times (3×455 kg) with a pre-mixed solution of water (325 kg) and acetonitrile (130 kg). The cake was dried at 50° C. and the dried cake was dissolved with ethyl acetate (1055 kg). The organic stream was charged with seeds (1.7 kg). A solution of methanesulfonic acid (28 kg) in ethyl acetate (453 kg) was charged over 2 h and the slurry was aged for 1 h. The shiny was then filtered and washed with ethyl acetate (3×320 kg). The cake was dried under vacuum at 50° C. to yield 124.8 kg of product in 90% yield, 99.94 HPLC area percent as a white solid.

$^1$H NMR (600 MHz, DMSO-$d_6$) δ 10.19 (s, 1H), 9.24 (d, J=5.7 Hz, 1H), 8.40 (dd, J=10.3, 2.6 Hz, 1H), 8.33 (dd, J=9.4, 5.3 Hz, 1H), 8.09 (d, J=5.7 Hz, 1H), 8.04 (t, J=8.6 Hz, 1H), 7.71-7.64 (m, 2H), 7.37-7.30 (m, 2H), 3.64 (ddt, J=10.8, 7.3, 3.8 Hz, 1H), 2.98-2.89 (m, 1H), 2.43 (s, 3H), 2.05-1.60 (m, 9H), 1.14 (d, J=6.7 Hz 3H); $^{13}$C NMR (150 MHz, DMSO-$d_6$) δ 175.0, 162.7, 161.1, 145.4, 138.2, 136.8, 128.6, 128.1, 126.7, 126.4, 123.3, 120.8, 119.8, 109.0, 39.8, 39.7, 38.6, 35.5, 28.3, 27.6, 27.2, 26.1, 16.2 HRMS (ESI): calculated for $C_{24}H_{25}ClFN_2O$ [M+H]$^+$; 410.1634; found, 410.1625.

Example 8

(R)—N-(4-chlorophenyl)-2-((1s,4S)-4-(6-fluoroquinolin-4-yl)cyclohexyl)propanamide Salts and Co-Crystals To a 10 L glass-lined reactor under a blanket of nitrogen was charged 349 g N,N,N',N'-tetramethylchloroformamidinium hexafluorophosphate (TCFH) and 2 L acetonitrile. 245 g N-methylimidazole was added followed by 0.3 L acetonitrile. 300 g (R)-2-((1s,4S)-4-(6-fluoroquinolin-4-yl)cyclohexyl)propanoic acid was added followed by 0.3 L acetonitrile. The mixture was held for 0.5 h then 139 g 4-chloroaniline charged followed by 0.4 L acetonitrile. The mixture was maintained at 20° C. until the reaction was deemed complete by HPLC analysis. The solution was then heated to 60° C., and 1.2 L water was charged. The solution was then cooled to 40° C., seeds (3 g) were charged, and the resulting slurry WM maintained for 1 h. The slurry was then cooled to 20° C. and 2.7 L water was charged. The slurry was filtered and the cake was washed three times with 3 L of 2:1 water:acetonitrile.

The cake is dissolved with about 5 L organic solvent and the solution is distilled to a volume of about 4 L at about 40° C. under vacuum. The slum is cooled to about 20° C., and a solution of an appropriate amount of an acid or co-crystal former in, e.g., water or an organic solvent is added. The slurry is then filtered and washed and dried to yield about 445 g of (R)—N-(4-chlorophenyl)-2-((1s,4S)-4-(6-fluoroquinolin-4-yl)cyclohexyl)propanamide salt or co-crystal.

Example 9

(R)—N-(4-chlorophenyl)-2-((1s,4S)-4-(6-fluoroquinolin-4-yl)cyclohexyl)propanamide methanesulfonate

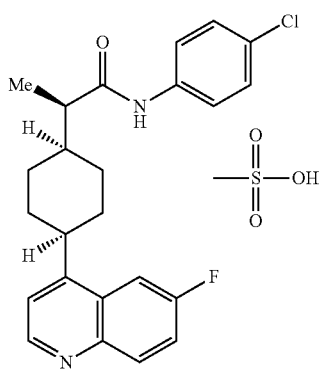

To a 10 L glass-lined reactor under a blanket of nitrogen was charged 349 g N,N,N',N'-tetramethylchloroformamidinium hexafluorophosphate (TCFH) and 2 L acetonitrile. 245 g N-methylimidazole was added followed by 0.3 L acetonitrile. 300 g (R)-2-((1s,4S)-4-(6-fluoroquinolin-4-yl)cyclohexyl)propanoic acid was added followed by 0.3 L acetonitrile. The mixture was held for 0.5 h then 139 g 4-chloroaniline charged followed by 0.4 L acetonitrile. The mixture was maintained at 20° C. until the reaction was deemed complete by HPLC analysis. The solution was then heated to 60° C., and 1.2 L water was charged. The solution was then cooled to 40° C., seeds (3 g) were charged, and the resulting slurry was maintained for 1 h. The slurry was then cooled to 20° C., and 2.7 L water was charged. The slurry was filtered and the cake was washed three times with 3 L of 2:1 water:acetonitrile. The cake was dissolved with 5.1 L ethyl acetate and the solution was distilled to a volume of 4.2 L at 41° C. under vacuum. The slurry was cooled to 20° C., 4.14 g seeds were charged, and a solution of 95.7 g methanesulfonic acid in 2.9 L ethyl acetate was added. The slurry was then filtered and washed two times with 1.65 L ethyl acetate and dried under vacuum at 50° C. to yield 445 g of (R)—N-(4-chlorophenyl)-2-((1s,4S)-4-(6-fluoroquinolin-4-yl)cyclohexyl)propanamide methanesulfonate as a white solid in 88% yield.

$^1$H NMR (600 MHz, DMSO-$d_6$) δ 10.19 (s, 1H), 9.24 (d, J=5.7 Hz, 1H), 8.40 (dd, J=10.3, 2.6 Hz, 1H), 8.33 (dd, J=9.4, 5.3 Hz, 1H), 8.09 (d, J=5.7 Hz, 1H), 8.04 (t, J=0.6 Hz, 1H), 7.71-7.64 (m, 2H), 7.37-7.30 (m, 2H), 3.64 (ddt, J=10.8, 7.3, 3.8 Hz, 1H), 2.98-2.89 (m, 1H), 2.43 (s, 3H), 2.05-1.60 (m, 9H), 1.14 (d, J=6.7 Hz, 3H); $^{13}$C NMR (126 MHz, DMSO-$d_6$) δ 175.0, 162.7, 161.1, 145.4, 138.2, 136.8, 128.6, 128.1, 126.7, 126.4, 123.3, 120.8, 119.8, 109.0, 39.8, 39.7, 38.6, 35.5, 28.3, 27.6, 27.2, 26.1, 16.2 MS (ESI): calcd for $C_{24}H_{24}ClFN_2O$ ([M+H]$^+$), 410.16; found, 410.15.

HPLC analysis: Column: Sigma-Aldrich Supelco Ascentis Express C18 2.7 um, 150×4.6 mm ID; Solvent A: 0.05% TFA with MeCN:water (5/95 v/v); Solvent B: 0.05% TFA with MeCN:water (95/5 v/v); Gradient: % B: 0 Min. 15%; 1 Min. 15%; 13 Min. 55%; 19 Min. 65%; 24 Min. 100%; 24.1 15%; 28 Min. 15%; Stop Time: 24 Min; Flow Rate: 1.0 ml/min; Column temperature: 30° C.; wavelength: 218 nm. The retention time (R)—N-(4-chlorophenyl)-2-((1s,4S)-4-(6-fluoroquinolin-4-yl)cyclohexyl)propanamide peak was 12.6 min.

Example 10 methyl (R)-2-((1s,4S)-4-(6-fluoroquinolin-4-yl)cyclohexyl)propanoate

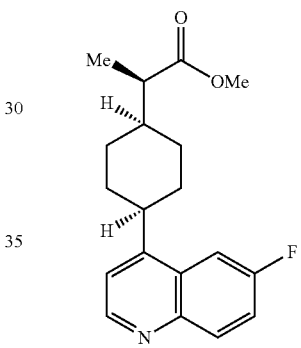

Methanol (300.0 mL) was charged to a 250-mL glass reactor followed by Y(OTf)$_3$ (0.606 g, 1.12 mmol) under protection of nitrogen then warmed to 60° C. for 1 h. (4R)-3-[(2R)-2-[4-(6-fluoro-4-quinolyl)cyclohexyl]propanoyl]-4-phenyl-oxazolidin-2-one (10.00 g, 22.40 mmol) was added all at once as a solid. The reaction mixture was then aged for 3 h. The reaction mixture was cooled to 30° C. and concentrated to dryness in vacuo.

$^1$H NMR (400 MHz, CDCl$_3$) δ 8.82 (d, 1H), 8.12 (dd, 1H), 7.75-7.62 (m, 1H), 7.54-7.43 (m, 1H), 7.35 (d, 1H), 3.71 (s, 3H), 3.36-3.20 (m, 1H), 2.89-2.72 (m, 1H), 2.05-1.91 (m, 2H), 1.90-1.63 (m, 7H), 1.21 (d, 3H); $^{13}$C NMR (100 MHz, CDCl$_3$) δ 177.2, 160.5 (d, 1C), 152.0 (d, 1C), 149.6, 145.6, 132.9 (d, 1C), 127.7 (d, 1C), 119.0 (d, 1C), 118.3, 106.7 (d, 1C), 51.5, 39.9, 38.3, 36.3, 29.4, 27.9, 27.7, 26.9, 15.7; LCMS ESI (+) m/z 316 (M+H). HPLC analysis: Column: Ascentis Express C18 2.7 um, 150×4.6 mm ID; Solvent A: 0.05% TFA in water:acetonitrile (95:5); Solvent B: 0.05% TFA in water:acetonitrile (5:95); Gradient: % B: 0 Min. 15%; 12 Min. 60%; 14 Min. 100%; 16 Min. 100%; Stop Time: 16 min; Flow Rate: 1 ml/min; wavelength: 218 nm. The retention time of methyl (R)-2-((1s,4S)-4-(6-fluoroquinolin-4-yl)cyclohexyl)propanoate was 9.2 min.

Example 11

(R)-2-((1s,4S)-4-(6-fluoroquinolin-4-yl)cyclohexyl)propanoic acid

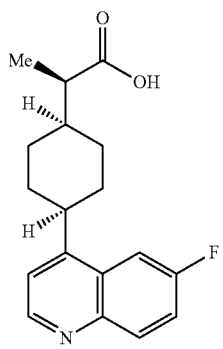

DMAC (50.0 mL) was charged to the crude methyl (R)-2-((1s,4S)-4-(6-fluoroquinolin-4-yl)cyclohexyl)propanoate at 30° C. followed by the addition of 5.0 M NaOH (13.0 mL, 65.0 mmol). The reaction mixture was allowed to stir for 20 h. A 50 wt % solution of citric acid (25.0 mL) was added slowly to adjust the pH. The reaction mixture was warmed to 70° C. followed by the addition of water (20 mL) over 2 h then a 1 h age. The slurry was cooled to 20° C. over 6 h then held overnight. The slurry was filtered, washed with 1:1 DMAC/water (30 mL), 1:3 MeCN/water (2×30 mL), then dried in a 50° C. oven with a nitrogen sweep. (R)-2-((1s,4S)-4-(6-fluoroquinolin-4-yl)cyclohexyl)propanoic acid (5.52 g, 18.3 mmol, 81.8% yield) was isolated as a white solid. $^1$H NMR (400 MHz, DMSO-$d_6$) δ 12.95 (br s, 1H), 8.80 (d, 1H), 8.08 (dd, 1H), 7.95 (dd, 1H), 7.65 (t, 1H), 7.50 (d, 1H), 3.38 (br 1H), 2.78-2.66 (m, 1H), 1.86-1.61 (m, 9H), 1.09 (d, 3H); $^{13}$C NMR (151 MHz, DMSO-$d_6$) δ 177.7, 159.9 (d, 1C), 152.2 (d, 1C), 149.8 (d, 1C), 145.1, 132.6 (d, 1C), 127.2 (d, 1C), 118.9 (d, 1C), 118.7, 107.1 (d, 1C), 39.1, 37.2, 35.7, 28.7, 27.8, 27.2, 26.2, 15.6; LCMS ESI (+) m/z 302 (M+H).

HPLC analysis: Column: Ascentis Express C18 2.7 um, 150×4.6 mm ID; Solvent A: 0.05% TFA in water:acetonitrile (95:5); Solvent B: 0.05% TFA in water:acetonitrile (5:95); Gradient: % B: 0 Min. 15%; 12 Min. 60%; 14 Min. 100%; 16 Min. 100%; Stop Time: 16 min; Flow Rate: 1 ml/min; wavelength: 218 nm. The retention time of (R)-2-((1s,4S)-4-(6-fluoroquinolin-4-yl)cyclohexyl)propanoic acid was 7.0 min.

Example 12

Preparation of

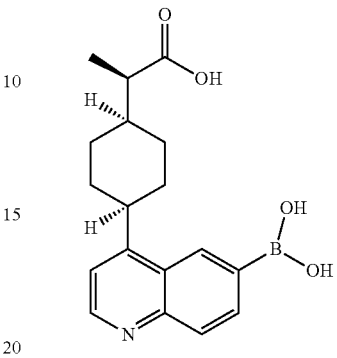

A clean 250 mL round bottom flask was charged with the compound from Example 11 (9.5 g, 30 mmol), tetrahydroxydiboron (7.28 g, 78.8 mmol) and a magnetic stir bar 100 mL methanol was added followed by N,N-diisopropylethylamine (19.4 mL, 110 mmol) and the solution was sparged for 20 min. In a separate 100 mL round bottom flask (RBF), nickel nitrate (0.463 g, 1.58 mmol) and tricyclohexylphosphonium tetrafluoroborate (1.29 g, 3.47 mmol) in 50 mL methanol were combined to give a pale green solution which was sparged for 20 min. After 20 min of sparging both solutions, the Ni/PCy3 solution was then cumulated into the 250 mL RBF. The combined mixture was sparged for another 45 min with magnetic stirring at RT. The mixture was then heated to 55° C. After 5 h and 15 minutes the mixture was cooled to rt and 35 mL TFA, 170 mL water, and 50 mL methanol were added. Then 400 mL heptane was added, the mixture was agitated, and the phases were separated. The rich aqueous layer was then loaded directly on to the column in 75 mL aliquots for purification. Column: Biotage Ultra C18 400 g, 25-micron spherical particles. Mobile phase A: 95/5/0.2 water/acetonitrile/TFA. Mobile phase B: acetonitrile. Gradient: 0-3.7 column volumes (CV) (1 CV=760 ml): 10-25% B (linear ramp), 50 ml/min, 3.7-4.8 CV: 90% B (hold), 50 ml/min, 4.8-5.8 CV: 10% B (hold), 50 ml/min. Fractions containing the desired product were combined and diluted with 7.4 L water and loaded in one portion on to the same column for solid phase extraction. The loaded column was washed with 95/5 water/acetonitrile and eluted with 100% THF. The fractions containing the desired product were combined and concentrated via rotary evaporation to yield 5.52 g of desired compound as a white solid in 56% yield. $^1$H NMR (600 MHz, DMSO-$d_6$) δ 12.14 (br s, 1H), 8.82 (d, J=4.6 Hz, 1H), 8.71 (s, 1H), 8.39 (br s, 2H), 8.10 (d, J=8.5 Hz, 1H), 7.96 (d, J=8.5 Hz, 1H), 7.45 (d, J=4.6 Hz, 1H), 3.63-3.44 (m, 2H), 2.76-2.67 (m, 1H), 1.87 (br d, J=10.3 Hz, 2H), 1.82-1.66 (m, 7H), 1.11 (d, J=6.7 Hz, 3H), 13C NMR (151 MHz, DMSO-d6) δ 177.8, 153.4, 150.8, 148.8, 133.8, 132.1, 130.2, 128.4, 125.7, 118.0, 39.1, 37.2, 35.7, 29.0, 28.1, 27.4, 26.5, 15.7. HRMS (ESI); calcd for C18H23O4NB ([M+H]+), 328.1715; found 328.1718.

Example 13

Preparation of

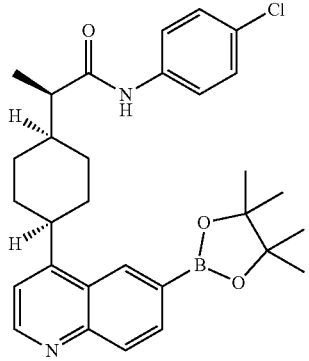

To a clean 25 mL round bottom flask was charged the compound of Example 12 (A, 0.500 g, 1.53 mmol), pinacol (0.190 g, 1.61 mmol), and tetrahydrofuran (5.00 mL, 61.4 mmol). The mixture was magnetically stirred at rt for 90 min. The mixture was then cooled to 0° C. and 1-methylimidazole (0.730 mL, 9.17 mmol) was added followed by propylphosphonic anhydride (1.67 mol/L) in ethyl acetate (4.58 mL, 7.65 mmol), and 4-chloroaniline (391.0 mg, 3.065 mmol). The reaction WO complete after 2 h and the entire mixture was poured into 25 mL sodium bicarbonate (1.03 mol/L) and water (15 mL, 832.649 mmol) that was pro-cooled to 0° C. Ethyl acetate (5 mL) was added and the phases split in a sep funnel. The aqueous layer was extracted again with ethyl acetate (40 mL, 400 mmol). The rich organics were combined and washed with 15 mL 1:1 saturated $NaHCO_3$(aq):water. The rich organics were then dried with 1 g $MgSO_4$ and filtered. The crude stream was then purified via column chromatography. Column: Biotage Ultra silica 25 g, 25-micron spherical particles. Mobile phase A: dichloromethane. Mobile phase B: ethyl acetate. Gradient: 0-20 CV (1 CV=33 ml): 30-100% EtOAc in DCM (linear ramp), 26 ml/min. Fractions containing the desired product were combined and concentrated via rotary evaporation to yield 369 mg of desired compound as a white solid in 59% yield. $^1$H NMR (600 MHz, DMSO-$d_6$) δ 10.11 (s, 1H), 8.92 (d, J=4.6 Hz, 1H), 8.50 (s, 1H), 8.01 (d, J=8.5 Hz, 1H), 7.95 (d, J=8.4 Hz, 1H), 7.68-7.64 (m, 2H), 7.56 (d, J=4.6 Hz, 1H), 7.35-7.32 (m, 2H), 3.46 (br t, J=10.9 Hz, 1H), 2.89-2.83 (m, 1H), 2.00-1.93 (m, 2H), 1.87 (br d, J=12.6 Hz, 1H), 1.78-1.59 (m, 6H), 1.33 (s, 12H), 1.13 (d, J=6.7 Hz, 3H), 13C NMR (126 MHz, DMSO-d6) δ 175.0, 170.3, 153.2, 151.4, 149.4, 138.1, 133.3, 130.4, 129.4, 128.5, 126.7, 125.6, 120.8, 118.5, 84.0, 59.7, 40.3, 37.2, 35.6, 28.6, 28.0, 27.6, 26.5, 24.7, 24.7, 20.7, 16.0, 14.1. HRMS (ESI): calcd for $C_{30}CH_{37}O_3N_2BCl$ ([M+H]+), 519.2580; found 519.2579.

Example 14

Preparation of

Automated synthesis using commercial Synthera synthesis module (IBA) and custom HPLC system. The automated synthesis of [$^{18}$F](R)—N-(4-chlorophenyl)-2-((1S,4S)-4-(6-fluoroquinolin-4-yl)cyclohexyl)propanamide was carried out using a cassette type IBA Synthera synthesis module with an appropriately assembled integrator fluidic processor kit for the reaction. Followed by transfer to a custom automated system for HPLC purification and reformulation. The integrator fluidic processor (IFP) kit and custom system were loaded with appropriate precursors for this synthesis and are summarized in the Table, below. Purification was performed on a Varian HPLC unit with filling of the injection loop controlled by a steady stream of nitrogen.

| | |
|---|---|
| Vial 1 (V1) | 6 mg potassium trifluoromethanesulfonate |
| | 1.5 mg potassium carbonate |
| | 0.5 mL of distilled water |
| | 1.0 mL of acetonitrile |
| QMA | Sep-Pak Accell Plus QMA Carbonate Plus Light Cartridge, 46 mg, 40 µM particle (Waters: PN 186004540) |
| | Pre-conditioned with: |
| | 1) 10 mL ethanol |
| | 2) 900 mg potassium trifluoromethanesulfonate in 10 mL distilled water |
| | 3) 10 mL of distilled water |
| Vial 2 (V2) | 2 mg (R)-N-(4-chlorophenyl)-2-((1S,4S)-4-(6-(4,4,5,5-tetramethyl-1,3,2-dioxaborolan-2-yl)quinolin-4-yl)cyclohexyl)propanamide |
| | 7 mg Copper(II) trifluoromethanesulfonate |
| | 40 µL pyridine |
| | 0.7 mL N,N-Dimethylformamide |
| Vial 4 (V4) | 2.5 mL of distilled water |
| | 1.5 mL acetonitrile |
| HPLC Column | Phenomenex Luna, 5 µm C 18(2) 100 Å, 250 × 10 mm (PN 00G-4252-N0) |
| HPLC Solvent | 40% acetonitrile in an aqueous 0.1% trifluoroacetitic acid solution |
| HPLC flow | 4.0 mL/min |
| Dilution Flask | 30 mL of distilled water |
| Cartridge | Phenomenex Strata C18-U (55 µM, 70 Å), 100 mg/1 mL Tube (PN 8B-S002-EAK) |
| | Pre-conditioned with: |
| | 5 mL ethanol |
| | 2) 10 mL distilled water |
| Vial 5 (V5) | 1 mL ethanol |
| Product Vial | 4 mL saline |

Aqueous [$^{18}$F] fluoride solution (2.0 ml, 59.2 GBq/1.6 Ci) was delivered to a Sep-Pak light 46 mg QMA that had been pre-conditioned After completion of the transfer, aqueous

[¹⁸F] fluoride was released from the QMA Sep-Pak by addition of the elution mixture (from "V1") into the reactor. The solvent was evaporated under a gentle stream of nitrogen and vacuum. Then a solution of precursor (from "V2") was added to the dried fluoride-18 and heated at 110° C. for 30 minutes. After it was diluted with 2.5 mL of distilled water and 1.5 mL of acetonitrile (from "V4") followed with transfer to an intermediate vial (to "Pre-HPLC").

The mixture was then loaded onto a 5 mL sample injection loop then to the semi-preparative HPLC column. A mixture of 40% acetonitrile in an aqueous 0.1% trifluoroacetic acid solution was flushed through the column at a rate of 4.0 mL per minute, pressure 1850 PSI, UV 220 nm. Product was isolated from 22 to 24 min into the dilution flask which contained 30 mL distilled water. The entire contents were transferred to a C18 solid phase extraction cartridge that was pre-activated then released with 1 mL of ethanol (from "V5") into the product vial of 4 mL saline, to create a 20% ethanol in saline solution for injection. 31.2 mCi (1.15 GBq) of [18F](R)—N-(4-chlorophenyl)-2-((1S,4S)-4-(6-fluoroquinolin-4-yl)cyclohexyl)propanamide.

This product was analyzed via reverse phase HPLC and the chemical identified by co-injection of non-radioactive reference standard of (R)—N-(4-chlorophenyl)-2-((1 S,4S)-4-(6-fluoroquinolin-4-yl)cyclohexyl)propanamide, radiochemical purity, chemical purity and specific activity. The isolated product that co-eluted with non-radioactive reference standard at 16 min was 99% radiochemically and 95% chemically pure, with a specific activity of 0.38 GBq/nmol (10.47 mCi/nmol). The product was analyzed via chiral HPLC: chiral purity by co-injection of non-radioactive reference standards (R)—N-(4-chlorophenyl)-2-((1S,4S)-4-(6-fluoroquinolin-4-yl)cyclohexyl)propanamide (10 min) and (S)—N-(4-chlorophenyl)-2-((1S,4S)-4-(6-fluoroquinolin-4-yl)cyclohexyl)propanamide (11.5 min). The isolated product co-eluted with the non-radioactive reference standard at 10 min with an ee: >99.5%.

What is claimed:

1. A method for preparing Compound 1, or a stereoisomer thereof,

Compound 1

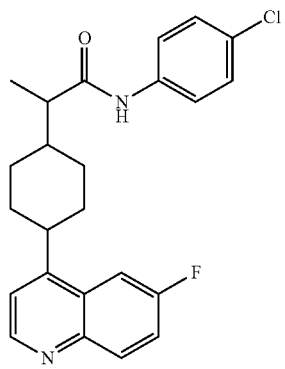

comprising:
contacting a compound of formula II, or a stereoisomer thereof:

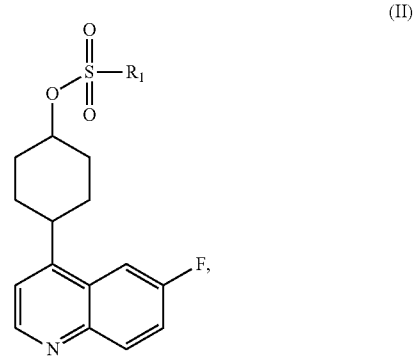

(II)

wherein $R_1$ is $C_{1-6}$alkyl, aryl, or $C_{1-6}$haloalkyl, with a mixture of a $C_{1-6}$alkoxide salt and a di-$C_{1-6}$alkyl-malonate, in a suitable organic solvent, for a time and at a temperature sufficient to displace the sulfonate moiety and to produce a compound of formula III, or a stereoisomer thereof:

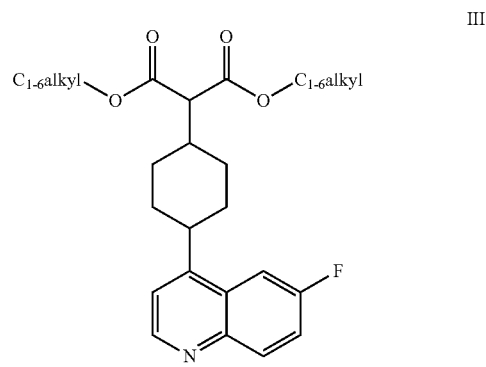

III and
contacting the compound of formula III, or a stereoisomer thereof, with a suitable organic acid, in a suitable aqueous organic solvent, for a time and at a temperature sufficient for hydrolysis and decarboxylation and to produce a compound of formula I, or a stereoisomer thereof

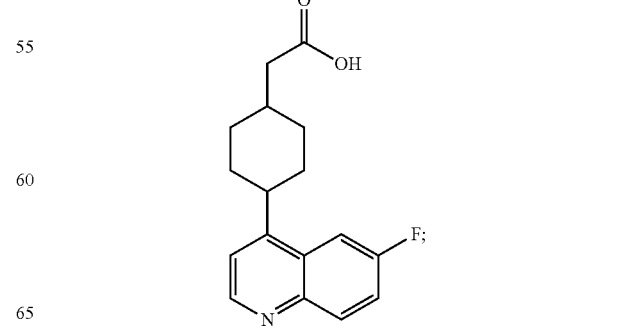

(I)

converting the compound of formula I, or a stereoisomer thereof,
to a Compound 2, or a stereoisomer thereof:

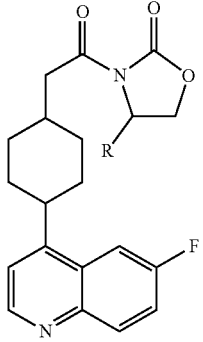

Compound 2 wherein R is phenyl or benzyl; and
converting the Compound 2, or a stereoisomer thereof, to a Compound 3, or a stereoisomer thereof

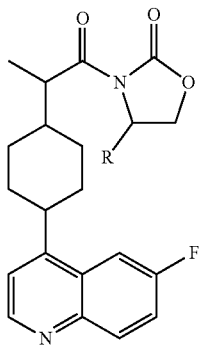

Compound 3 and
converting the Compound 3, or a stereoisomer thereof, to a Compound 4, or a stereoisomer thereof and

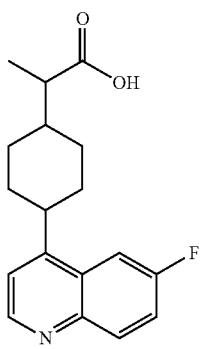

Compound 4 and
converting the Compound 4, or a stereoisomer thereof, to the Compound 1, or a stereoisomer thereof; and
optionally preparing a pharmaceutically acceptable salt or co-crystal of the Compound 1.

2. The method of claim 1, wherein the Compound 1 is

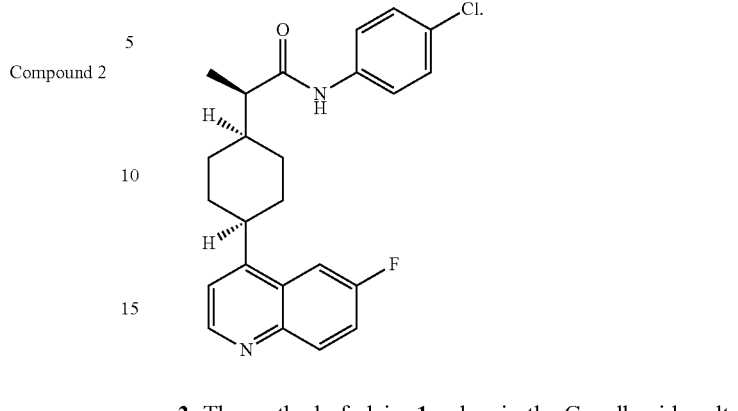

3. The method of claim 1, wherein the $C_{1-6}$alkoxide salt is sodium t-amylate and the di-$C_{1-6}$alkyl-malonate is di-tert-butyl malonate.

4. The method of claim 1, wherein the organic acid is methanesulfonic acid.

5. The method of claim 1, wherein $R_1$ is methyl.

6. The method of claim 1, wherein the compound of formula II, or a stereoisomer thereof, is prepared by contacting a compound of formula IV:

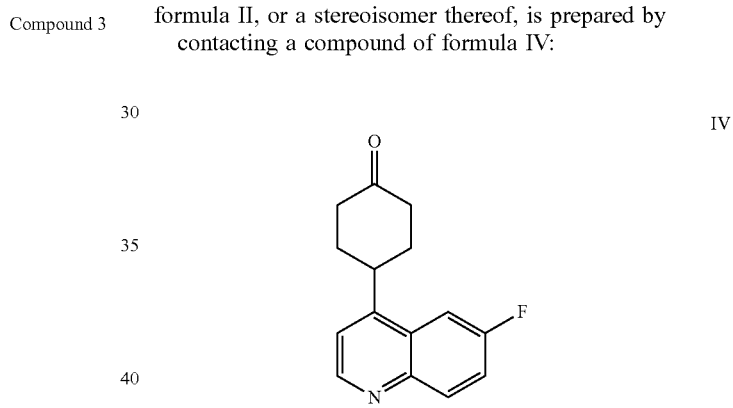

IV with a Lewis acid and a hydride source, in a suitable alcoholic organic solvent, for a time and at a temperature sufficient to reduce the carbonyl and to produce a compound of formula V, or a stereoisomer thereof:

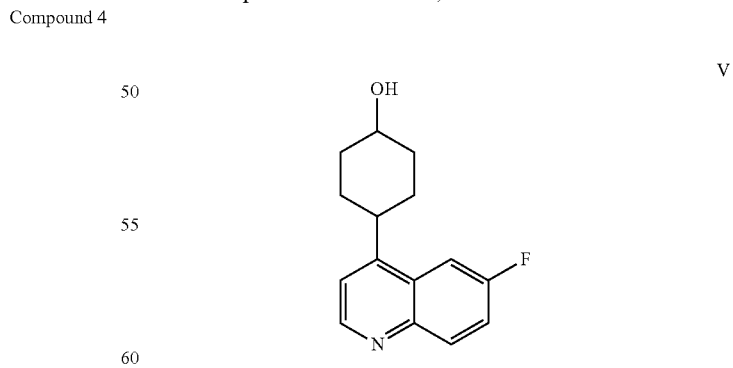

V and
contacting the compound of formula V, or a stereoisomer thereof, with X—$SO_2$—$R_1$,
wherein X is halo, or with $R_1$—$SO_2$—O—$SO_2$—$R_1$ in the presence of an alkyl-amine base, in a suitable anhydrous organic solvent, for a time and at a temperature sufficient for X displacement to produce the compound of formula II, or a stereoisomer thereof.

7. The method of claim 6, wherein the Lewis acid is CeCl₃, or a hydrate thereof, and the hydride source is NaBH₄.

8. The method of claim 6, wherein X is Cl and $R_1$ is methyl.

9. The method of claim 6, wherein the alkyl-amine base is Et₃N.

10. The method of claim 6, wherein the compound of formula IV is prepared by contacting a compound of formula VI-A or VI-B:

VI-A

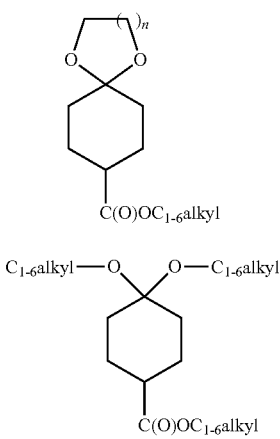

VI-B

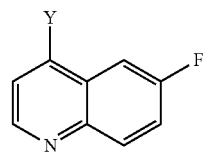

wherein n is 1 or 2; with a compound of formula VII

VII

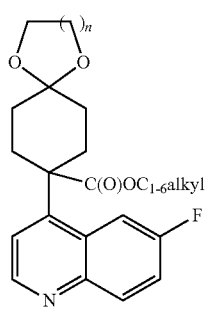

wherein Y is halo;
in the presence of a suitable $C_{1-6}$alkylsilylamine base, in a suitable organic solvent, for a time and at a temperature sufficient for Y displacement to produce a compound of formula VIII-A or formula VIII-B;

VIII-A

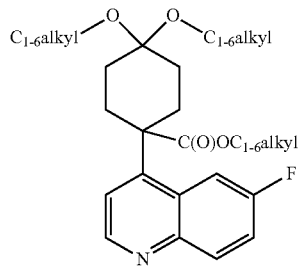

VIII-B and
contacting the compound of formula VIII-A or formula VIII-B with a suitable hydroxide base, in a suitable aqueous solvent, for a time and at a temperature sufficient for hydrolysis to produce a compound of formula IX-A or formula IX-B;

IX-A

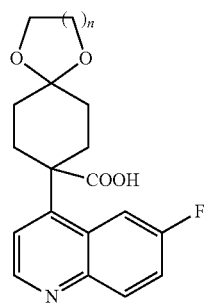

IX-B

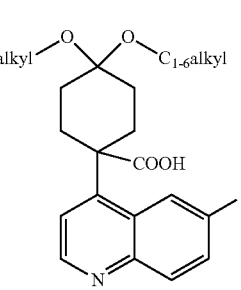

and
contacting the compound of formula IX-A or formula IX-B, with a suitable mineral acid, in a suitable aqueous solvent, for a time and at a temperature sufficient for hydrolysis and decarboxylation to produce the compound of formula IV.

11. The method of claim 10, wherein n is 1.

12. The method of claim 10, wherein Y is Cl.

13. The method of claim 10, wherein the $C_{1-6}$alkylsilylamine is NaHMDS.

14. The method of claim 10, wherein the hydroxide base is KOH or NaOH.

15. The method of claim 10, wherein the mineral acid is HCl.

16. The method of claim 1, wherein the compound of formula I is:
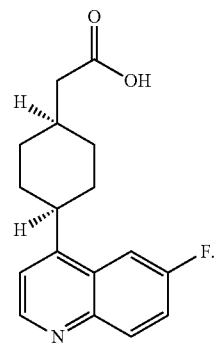 [SMILES: O=C(O)C[C@H]1CC[C@@H](c2ccnc3ccc(F)cc32)CC1]
17. The method of claim 1, wherein the compound of formula II is:
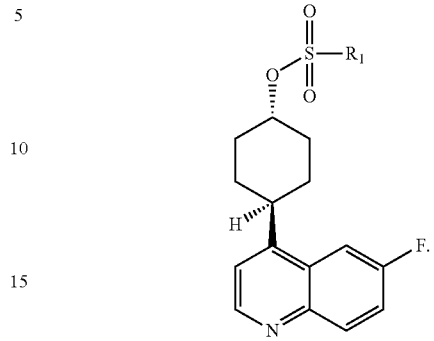
* * * * *

UNITED STATES PATENT AND TRADEMARK OFFICE
CERTIFICATE OF CORRECTION

PATENT NO. : 11,919,863 B2
APPLICATION NO. : 17/552929
DATED : March 5, 2024
INVENTOR(S) : Albert J. Delmonte et al.

It is certified that error appears in the above-identified patent and that said Letters Patent is hereby corrected as shown below:

In the Claims

Under Column no. 63, Claim no. 1, Line no. 44, Replace:
"stereoisomer thereof and"
With:
--stereoisomer thereof--

Signed and Sealed this
Thirtieth Day of July, 2024

Katherine Kelly Vidal
*Director of the United States Patent and Trademark Office*